United States Patent
Craighead et al.

(10) Patent No.: US 9,605,298 B2
(45) Date of Patent: *Mar. 28, 2017

(54) DEVICE AND METHODS FOR MOLECULAR ANALYSIS

(75) Inventors: Harold G. Craighead, Ithaca, NY (US); Benjamin R. Cipriany, Wappingers Falls, NY (US); Stephen Levy, Ithaca, NY (US); Paul Soloway, Ithaca, NY (US)

(73) Assignee: Cornell University, Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/389,259

(22) PCT Filed: Aug. 6, 2010

(86) PCT No.: PCT/US2010/044810
§ 371 (c)(1),
(2), (4) Date: May 14, 2012

(87) PCT Pub. No.: WO2011/017681
PCT Pub. Date: Feb. 10, 2011

(65) Prior Publication Data
US 2012/0245047 A1    Sep. 27, 2012

Related U.S. Application Data

(60) Provisional application No. 61/231,979, filed on Aug. 6, 2009, provisional application No. 61/231,963, filed
(Continued)

(51) Int. Cl.
*C12Q 1/68*     (2006.01)
*B01L 3/00*     (2006.01)

(52) U.S. Cl.
CPC ......... *C12Q 1/68* (2013.01); *B01L 3/502761* (2013.01); *C12Q 1/6827* (2013.01);
(Continued)

(58) Field of Classification Search
USPC ............................................. 506/7
See application file for complete search history.

(56) References Cited

U.S. PATENT DOCUMENTS 6,221,654 B1    4/2001   Quake et al.
6,833,242 B2    12/2004  Quake et al.
(Continued)

FOREIGN PATENT DOCUMENTS

WO    WO 03/100101 A1    12/2003
WO    WO 2004/025266 A2   3/2004
(Continued)

OTHER PUBLICATIONS

Fu, Anne Y. et al., "An Integrated Microfabricated Cell Sorter," Jun. 1, 2002, Analytical Chemistry, vol. 74, No. 11, pp. 2451-2457.*
(Continued)

*Primary Examiner* — Robert T Crow
(74) *Attorney, Agent, or Firm* — Wilson Sonsini Goodrich & Rosati

(57) ABSTRACT

Systems and methods are provided for high speed sorting of objects in a continuous body of fluid. The object can be analyzed within one or more interrogation volumes that allow for simultaneous or time-correlated measurement of the object's properties. A processor can interpret the properties of the object and then measured and then direct the object to one of a plurality of downstream flow paths. In some embodiments, the sorting of the object is based on two or more properties of the object. The sorting process can be repeated to create a network of sorting events.

23 Claims, 24 Drawing Sheets

Related U.S. Application Data on Aug. 6, 2009, provisional application No. 61/307,827, filed on Feb. 24, 2010, provisional application No. 61/359,266, filed on Jun. 28, 2010.

(52) U.S. Cl.
CPC ............... *B01L 2200/0663* (2013.01); *B01L 2300/0654* (2013.01); *C12Q 2537/164* (2013.01); *C12Q 2565/629* (2013.01); *C12Q 2565/631* (2013.01)

(56) References Cited

U.S. PATENT DOCUMENTS

| | | | |
|---|---|---|---|
| 6,927,065 | B2 | 8/2005 | Chan et al. |
| 7,267,797 | B1 | 9/2007 | Craighead et al. |
| 7,312,085 | B2 * | 12/2007 | Chou et al. ............... 436/43 |
| 7,371,520 | B2 | 5/2008 | Zhao et al. |
| 7,402,422 | B2 | 7/2008 | Fuchs et al. |
| 7,405,434 | B2 | 7/2008 | Stavis et al. |
| 8,735,065 | B2 * | 5/2014 | Craighead ......... B01L 3/502761 435/6.11 |
| 9,447,451 | B2 * | 9/2016 | Craighead ......... B01L 3/502761 |
| 2003/0138829 | A1 * | 7/2003 | Unger et al. .................. 435/6 |
| 2005/0123947 | A1 | 6/2005 | Quake et al. |
| 2005/0207940 | A1 | 9/2005 | Butler et al. |
| 2006/0228747 | A1 | 10/2006 | Fuchs et al. |
| 2007/0003442 | A1 * | 1/2007 | Link et al. .................. 422/99 |
| 2007/0154895 | A1 | 7/2007 | Spaid et al. |
| 2007/0161028 | A1 | 7/2007 | Schwartz et al. |
| 2008/0014589 | A1 * | 1/2008 | Link et al. .................. 435/6 |
| 2008/0160622 | A1 | 7/2008 | Su et al. |
| 2009/0050542 | A1 | 2/2009 | Leary et al. |
| 2009/0234202 | A1 | 9/2009 | Goix et al. |
| 2012/0244532 | A1 | 9/2012 | Craighead et al. |
| 2014/0322710 | A1 | 10/2014 | Craighead et al. |

FOREIGN PATENT DOCUMENTS

| | | |
|---|---|---|
| WO | WO 2006/083907 A2 | 8/2006 |
| WO | WO 2007/109412 A2 | 9/2007 |
| WO | WO 2009/029957 A1 | 3/2009 |
| WO | WO 2010/044932 A2 | 4/2010 |
| WO | WO 2010/044932 A3 | 8/2010 |
| WO | WO 2010/129787 A2 | 11/2010 |

OTHER PUBLICATIONS

Dittrich, Petra S., "An Integrated Microfluidic System for Reaction, High-Sensitivity Detection, and Sorting of Fluorescent Cells and Particles," Analytical Chemistry, Nov. 1, 2003, vol. 75, No. 21, pp. 5767-5774.*
Stavis, Samuel et al., "Single molecule studies of quantum dot conjugates in a submicrometer fluidic channel," Jan. 13, 2005, Lab on a Chip, 5, pp. 337-343.*
Fraga, Mario et al., "DNA Methylation: A Profile of Methods and Applications," Sep. 2002, BioTechniques, 33, pp. 632-649.*
Anway, et al. Epigenetic transgenerational actions of endocrine disruptors and male fertility. Science. Jun. 3, 2005;308(5727):1466-9.
Barski, et al. High-resolution profiling of histone methylations in the human genome. Cell. May 18, 2007;129(4):823-37.
Bernstein, et al. A bivalent chromatin structure marks key developmental genes in embryonic stem cells. Cell. Apr. 21, 2006;125(2):315-26.
Bernstein, et al. The mammalian epigenome. Cell. Feb. 23, 2007;128(4):669-81.
Cipriany, et al. Single molecule epigenetic analysis in a nanofluidic channel. Anal Chem. Mar. 15, 2010;82(6):2480-7.
Feinberg. Phenotypic plasticity and the epigenetics of human disease. Nature. May 24, 2007;447(7143):433-40.

Fielder, et al. Dielectrophoretic sorting of particles and cells in a microsystem. Anal Chem. May 1, 1998;70(9):1909-15.
Han, et al. Entropic Trapping and Escape of Long DNA Molecules at Submicron Size Constriction. Physical Review Letters. Aug. 23, 1999; 83(8):1688-1691.
International search report and written opinion dated Apr. 15, 2011 for PCT Application No. US2010/044810.
International search report and written opinion dated Apr. 22, 2011 for PCT Application No. US2010/044806.
Jamieson, et al. Drug discovery with engineered zinc-finger proteins. Nat Rev Drug Discov. May 2003;2(5):361-8.
Jenuwein, et al. Translating the histone code. Science. Aug. 10, 2001;293(5532):1074-80.
Klose, et al. Genomic DNA methylation: the mark and its mediators. Trends Biochem Sci. Feb. 2006;31(2):89-97. Epub Jan. 5, 2006.
Luger, et al. Crystal structure of the nucleosome core particle at 2.8 A resolution. Nature. 1997; 389:251-260.
Mikkelsen, et al. Genome-wide maps of chromatin state in pluripotent and lineage-committed cells. Nature. Aug. 2, 2007;448(7153):553-60. Epub Jul. 1, 2007.
Moscou, et al. A simple cipher governs DNA recognition by TAL effectors. Science. Dec. 11, 2009;326(5959):1501.
Nielsen, et al. Sequence-selective recognition of DNA by strand displacement with a thymine-substituted polyamide. Science. Dec. 6, 1991;254(5037):1497-500.
O'Neill, et al. Epigenetic characterization of the early embryo with a chromatin immunoprecipitation protocol applicable to small cell populations. Nat Genet. Jul. 2006;38(7):835-41. Epub Jun. 11, 2006.
Ren, et al. Genome-wide location and function of DNA binding proteins. Science. Dec. 22, 2000;290(5500):2306-9.
Urnov, et al. Highly efficient endogenous human gene correction using designed zinc-finger nucleases. Nature. Jun. 2, 2005;435(7042):646-51. Epub Apr. 3, 2005.
Waterland, et al. Transposable elements: targets for early nutritional effects on epigenetic gene regulation. Mol Cell Biol. Aug. 2003;23(15):5293-300.
Weaver, et al. Epigenetic programming by maternal behavior. Nat Neurosci. Aug. 2004;7(8):847-54. Epub Jun. 27, 2004.
Weber, et al. Chromosome-wide and promoter-specific analyses identify sites of differential DNA methylation in normal and transformed human cells. Nat Genet. Aug. 2005;37(8):853-62. Epub Jul. 10, 2005.
Zhang, et al. Genome-wide high-resolution mapping and functional analysis of DNA methylation in arabidopsis. Cell. Sep. 22, 2006;126(6):1189-201. Epub Aug. 31, 2006.
Streng, D. E. The Nanofluidic Analysis of Chromatin. NCSU Libraries. Jul. 16, 2009.
Office action dated Feb. 9, 2016 for U.S. Appl. No. 14/260,082.
Office action dated Mar. 4, 2014 for CN 201080038285.8 (in English).
U.S. Appl. No. 14/260,082, filed Apr. 23, 2014, Craighead et al.
Paradowska, et al. Aberrant epigenetic modifications in the CTCF binding domain of the IGF2/H19 gene in prostate cancer compared with benign prostate hyperplasia. Int J Oncol. Jul. 2009;35(1):87-96.
Notice of allowance dated Jan. 9, 2014 for U.S. Appl. No. 13/367,300.
Office action dated Sep. 9, 2015 for U.S. Appl. No. 14/260,082.
Austin, R. Nanopores: The art of sucking spaghetti. Nat Mater. Sep. 2003;2(9):567-8.
Baret, et al. Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Chan, et al. DNA mapping using microfluidic stretching and single-molecule detection of fluorescent site-specific tags. Genome Res. Jun. 2004;14(6):1137-46.
European search report and search opinion dated Apr. 5, 2013 for EP Application No. 10807270.
Foquet, et al. DNA fragment sizing by single molecule detection in submicrometer-sized closed fluidic channels. Anal Chem. Mar. 15, 2002;74(6):1415-22.

(56) References Cited

OTHER PUBLICATIONS

Jurney, P. Nano and Microfluidics for Single Molecule Biophysics Applications. NNIN REU Research Accomplishments. 2008;pp. 20-21.
Office action dated Apr. 19, 2013 for U.S. Appl. No. 13/367,300.
Office action dated Sep. 11, 2013 for U.S. Appl. No. 13/367,300.
European search report and search opinion dated Jul. 1, 2016 for EP Application No. 10807274.5.
Notice of allowance dated May 20, 2016 for U.S. Appl. No. 14/260,082.

* cited by examiner

A.

B.

Figure 10A
Figure 10B
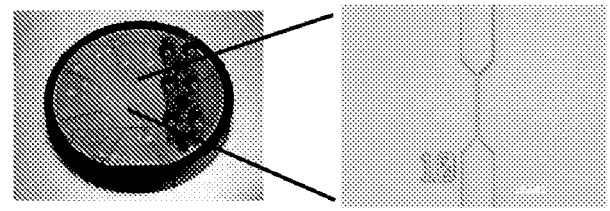
Fused Silica Wafer Stack with 27 Fluidic Channel Arrays
Fluidic Channel
500 nm (w)
250 nm (d)
Figure 10C
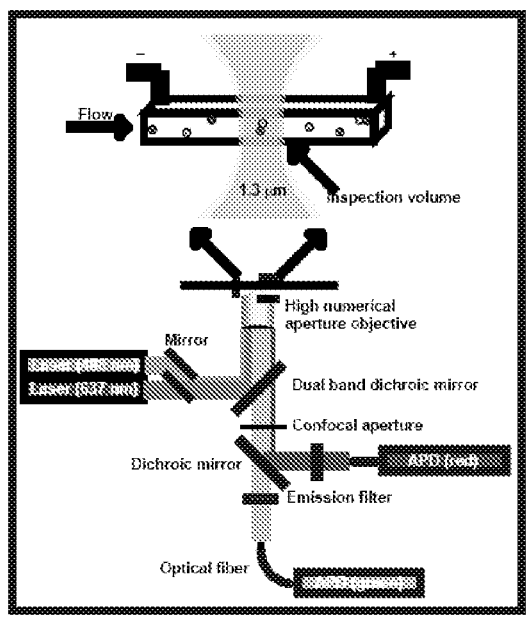
Figure 10D
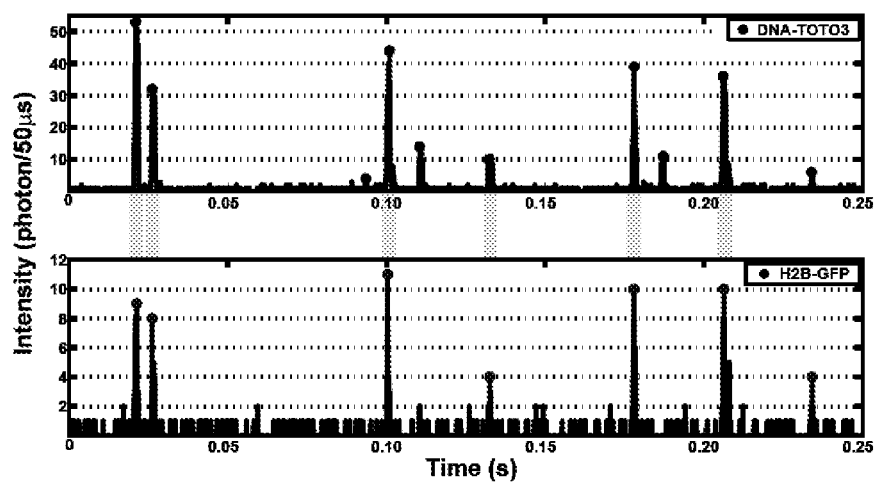

Figure 11A
Figure 11B
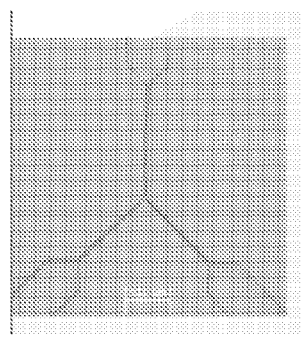
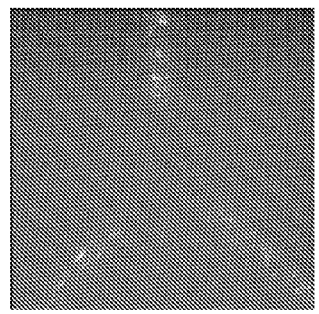
Figure 11C
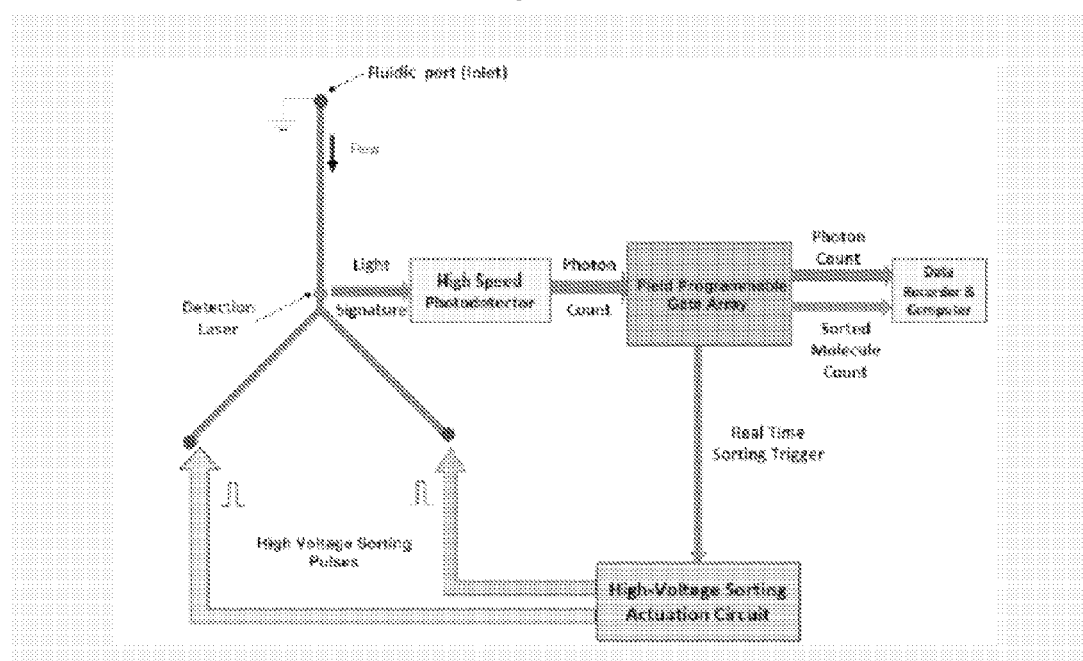

Figure 12A

| Applied Voltage (V) | Duration (min) | Qty Collected (fg) | Events (molecules/min) | Estimated Throughput (fg) | Collection Efficiency (%) |
|---|---|---|---|---|---|
| 100 | 0 | 0.6 ± 0.5 | - | - | - |
| 100 | 62 | 16.0 ± 1.2 | 172 ± 17 | 66 | 24.2 |
| 100 | 110 | 29.0 ± 2.1 | 169 ± 25 | 116 | 25 |
| 500 | 100 | 318.0 ± 9.6 | 2497 ± 88 ** | 1504 | 21.1 |

Native Chromatin and DNA Methylation Analyses:

| MNase Treatment (min) | 5 | 15 |
|---|---|---|
| DNA Concentration (pM)[b] | 588 ± 8 | 248 ± 2 |
| Dual-Labeled Chromatin (molecules/min)[a] | 1067 ± 114 | 201 ± 36 |
| H2B (molecules/min)[a] | 2116 ± 143 | 568 ± 67 |
| DNA (molecules/min)[a] | 6238 ± 611 | 2287 ± 184 |
| Average Fragment Size (bp)[c] | 1600 | 500 |
| DNA Throughput (Mbp/min)[d] | 10 | 1 |

Operational Frequency Dominates System Performance

Figure 18
Channel Resistive Characteristics
$$R_{fluidicCH} = \rho[(\frac{L_{mc}}{A_{mc}}) + (\frac{L_{nc}}{A_{nc}})]$$
$\rho$ = 10 ohm-m (1x TBE)
$\rho$ =  2 ohm-m (5x TBE)
$L_{mc}$ =  10 mm
$A_{mc}$ = 2.5x10$^{-4}$ mm x 1x10$^{-2}$ mm
$L_{nc}$ = 2x10$^{-2}$ mm
$A_{nc}$ = 2.5x10$^{-4}$ mm x 5.0x10$^{-4}$ mm
$R_{mc}$ = 40 G$\Omega$
$R_{nc}$ = 1.6 G$\Omega$
Figure 19
Star to Delta Network
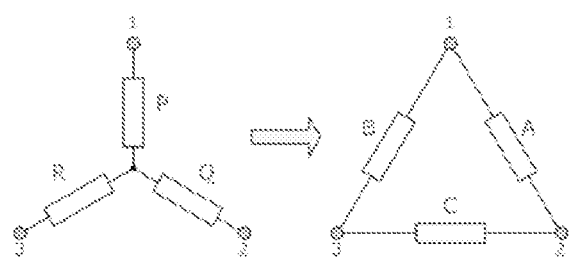
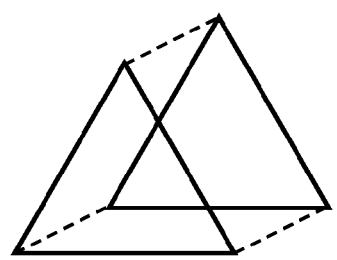

10 μm    15 mm    70 mm

Input-Output Resistive Unbalance -> Counter-Propagating Flows (Backflow)

Output-Output Resistive Unbalance -> Constant Partial Flow in Inactive Channel

Sorting Conditions:
-100 μs bin
-50 Volts applied
-280 μW per laser spot
-Sorting Threshold > 150 photons/bin
-RC Time Constant ~ 1 millisecond Results for Molecules with > 150 ph/bin:
-26 molecules observed (input)
-23 molecules identified in real time as satisfying sorting threshold (sort)
-9 molecules sorted (output)

Reed Relay
(Miniturized Mechanical Relay)

1. 1 ms switch response
2. 100 million cycle failure lifetime
3. Handles upto 100 volts
4. Off-State Leakage current < 100 pA Solid State Relay
(Transistor-Based Relay)

1. 0.2-0.5 ms switch response
2. No mechanical failure lifetime
3. Handles upto 200 volts
4. Off-State Leakage current ~ 1-10 nA Channel Resistive Characteristics
(ignoring reservoir contributions)

$$R_{fluidicCH} = \rho[(\frac{L_{mc}}{A_{mc}}) + (\frac{L_{nc}}{A_{nc}})]$$

$\rho$ = 1.3 ohm-m (5x TBE)
$L_{mc}$ = 10,300 µm
$A_{mc}$ = 0.25 µm x 40 µm
$L_{nc}$ = 52.5 µm
$A_{nc}$ = 0.25 µm x 0.50 µm In experiment we find:
$V_{applied}$ = 10 V
$I_{measured}$ = 120 pA
$R_{measured}$ = 83 GΩ

$R_{mc}$ = 1.34 GΩ
$R_{nc}$ = 0.55 GΩ
$R_{total}$ = 1.89 GΩ

$\rho$ = 6.3-6.7 ohm-m
(reported in literature for 1x TBE)

(axes shifted to illustrate time correlation)

DEVICE AND METHODS FOR MOLECULAR ANALYSIS

CROSS-REFERENCE

This application claims benefit of priority to U.S. Provisional Application No. 61/231,979, filed Aug. 6, 2009, U.S. Provisional Application No. 61/307,827, filed Feb. 24, 2010, U.S. Provisional Application No. 61/231,963, filed Aug. 6, 2009, and U.S. Provisional Application No. 61/359,266, filed Jun. 28, 2010, and the co-pending case PCT Patent Appl. No. PCT/US10/44806, filed herewith, each of which is incorporated herein by reference in its entirety for all purposes.

STATEMENT AS TO FEDERALLY SPONSORED RESEARCH

This invention was made with the support of the United States government under Contract number R01 DA025722 by the National Institutes of Health and Contract number ECS-9876771 by the National Science Foundation (NBTC).

BACKGROUND OF THE INVENTION

Separation of mixtures of complex biomolecules is an important element in high-throughput screening. The ability to sort biomolecules is particularly important in the fields of genomics, proteomics, and drug screening. In proteomics, for example, a vast diversity of (~10,000 different species) protein and peptide samples need to be separated and analyzed. One goal of proteomics is to rapidly identify and quantitate all of the proteins expressed in a cell or a specific subset of proteins expressed in a cell that are associated with a particular pathway or disease. Similarly in genomics, the ability to analyze and separate a large number of genome fragments rapidly is highly desirable. One goal of genomics is to rapidly identify and quantitate all of the genomic modifications in a cell or any similarly small sample such as laser microcaptured biological samples. One goal of drug screening is to identify small molecules that bind to a cellular or extracellular protein which serves as the target for therapeutic intervention (e.g. a drug or other therapeutic treatment). Molecules that bind to a target protein (e.g. small organic molecules, peptides, or macromolecules such as proteins and aptamers) often modulate their activity. Such molecules themselves can serve as therapeutics or can guide the design of therapeutics. Current sorting techniques such as column purification, immunoprecipitation, or gel electrophoresis suffer from a number of profound drawbacks including low sensitivity, low speed and high cost.

Thus there remains a considerable need for alternative tools useful for robust high-throughput applications in genomics, proteomics, drug screening and aptamer selection.

SUMMARY OF THE INVENTION

Single molecule studies of epigenetic state have the potential to access information currently unavailable with chromatin immunoprecipitation (ChIP), which has been limited to the study of one epigenetic mark at a time using microgram quantities of starting material. Conventional CHIP techniques have been described in Arnab Mukhopadhyay, Bart Deplancke, Albertha J M Walhout & Heidi A Tissenbaum, Nature Protocols 3, 698-709 (2008).

Accordingly, the present invention addresses the need for methods and devices for sorting of complex molecules with single molecule resolution. Single molecule detection in nanofluidics can eliminate the repetitive, serial preparations necessary to examine multiple epigentic marks. Multi-color signature of each molecule can be used to assess the presence of multiple marks simultaneously. This can allow the complex, interconnected roles of epigenetic marks to be understood and examined on picogram quantities of input material.

The invention provides for systems for sorting an object comprising: (a) a channel that is fluidically connected to a plurality of downstream flow paths, said channel being adapted to hold said object in a continuous liquid body in said channel; (b) one or more light sources configured to illuminate the channel to create one or more interrogation volumes; (c) a detection module configured to detect at least two types of signals indicative of two distinct properties of the object in the one or more interrogation volumes; and (d) a sorting module configured to direct the object to one of the plurality of downstream flow paths based on said two types of signals.

In some embodiments, the system can further comprise (a) one or more secondary light sources configured to illuminate one of the plurality of downstream flow paths to create one or more downstream interrogation volumes; and (b) a secondary detection module configured to detect at least one type of signals in the one or more downstream interrogation volumes. The system can also further comprise a secondary sorting module configured to direct the object to one of a plurality of secondary downstream flow paths based on said two types of signals in the one or more downstream interrogation volumes.

In any of the foregoing embodiments, the object is selected from the group consisting of a nucleic acid molecule, a protein, a chromatin, a biological molecule, a cell, a cellular component, a carbohydrate, and a genetic material. The one or more interrogation volumes can be less than 10, 1, 0.5, 0.2, 0.1, or 0.05 femtoliters. The channel can be fluidically connected to 2, 3, 4, or 5 downstream flow paths at a branch point. The system can comprise a plurality of interrogation volumes that are illuminating by a single light source. The system can comprise at least three interrogation volumes that are positioned along a straight line. The one or more light sources can create a plurality of interrogation volumes. The channel can be a microfluidic channel. The object can be carried by a fluid. The channel can comprise an optically transparent wall. The detection module can comprise one or more optical detectors. The object can flow through said continuous liquid body by way of electrokinetic force. The sorting module can comprise a plurality of electrodes configured to direct the object to the one of the plurality of downstream flow paths. The sorting module can comprise a plurality of electrodes configured to direct the object to the one of the plurality of downstream flow paths, wherein the electrodes are placed next to the switching volume by a distance of up to about 0.1, 1, or 10 mm. The sorting module can comprise one or more valves configured to direct the object to the one of the plurality of downstream flow paths. The sorting module can comprise optical tweezers. The sorting module can direct the object along with a switching fluid no greater than about 100, 10, 1, 0.5, or 0.1 femtoliters. The sorting module can direct the object along with a switching fluid no greater than about 100, 50, or 10 times the one or more interrogation volumes.

In any of the foregoing embodiments, the sorting module comprises a field-programmable gate array configured to receive data on the object and/or return instructions to direct the object to one of the plurality of downstream flow paths. The field-programmable gate array can interpret the data and/or return instructions in less than about $1\times10^{-3}$, $1\times10^{-4}$, $1\times10^{-5}$, $1\times10^{-6}$, or $1\times10^{-7}$ seconds.

Another aspect of the invention provides for methods for sorting an object in a channel, comprising: (a) flowing the object through said channel, wherein said object is labeled with a plurality of labels; (b) illuminating the channel to create a one or more interrogation volumes, each of which is confined by walls of said channel and a beam of light; and (c) detecting at least one label and another other label of said plurality in the same or distinct interrogation volumes of said one or more interrogation volumes to generate time-correlated resolution of said first and second label; and (d) directing the object to one of a plurality of downstream flow paths that are fluidically connected to said channel.

In some embodiments, the methods further comprise (a) illuminating a downstream pathway to create one or more downstream interrogation volumes; and (b) detecting at least one label of said plurality in the one or more downstream interrogation volumes. The methods can further comprise directing the object to one of a plurality of secondary downstream flow paths based on said detecting at least one label in the one or more downstream interrogation volumes.

In any of the foregoing embodiments, the object can be selected from the group consisting of a nucleic acid molecule, a protein, a chromatin, a biological molecule, a cell, a cellular component, a carbohydrate, and a genetic material. The channel can be illuminated to create a plurality of interrogation volumes. The object can be labeled with a plurality of labels. The methods can comprise detecting more than two distinct labels. The one or more interrogation volumes can be less than about 10, 1, 0.5, 0.2, 0.1, or 0.05 femtoliters. The labels are detected optically. The directing step is effected by electrokinetic force, an optical tweezer, or a valve. The object can be analyzed and directed in less than about 1, 0.5, 0.1, 0.01, 0.001, or 0.0001 seconds. The object can be directed to one of at least 2, 3, 4, or 5 downstream flow paths that are fluidically connected to the channel at a branch point. The object can be directed to the one of the plurality of downstream flow paths with a switching volume of less than about 100, 50, or 10 times the one or more interrogation volumes. The object can be directed to the one of the plurality of downstream flow paths with a switching volume that is less than about 1000, 100, 50, or 10 times the volume of the object. The one of a plurality of downstream flow paths can be chosen by a field-programmable gate array configured to receive data on the object and/or return instructions to direct the object to one of the plurality of downstream flow paths.

In one embodiment, the present invention provides a device comprising a microfluidic pathway configured for movement of a plurality of molecules in at least two defined directions, wherein said pathway comprises a submicrometer channel region, wherein said submicrometer channel region is configured for simultaneous interrogation of a single molecular property or a plurality of molecular properties of said molecules within said submicrometer channel region, and wherein said interrogation provides time dependent single molecule resolution. The submicrometer channel can comprises a width of less than about 1 µm and/or a height of less than about 1 µm. The submicrometer channel can have a length of between about 5 µm and about 500 µm. The device can comprise a submicrometer channel, where a portion of said submicrometer channel region is optically transparent. In a further aspect of any one of the foregoing embodiments, the present invention provides a device, wherein said device comprises fused silica or fused quartz.

In a further aspect of the foregoing embodiment, the present invention provides a device, wherein said molecules comprise one or more of polynucleotides, proteins, peptides, aptamers, organic molecules, small organic molecules, or candidate therapeutic molecules. The device can be configured to detect binding between two molecules or macromolecules or epigenetic modifications. The device can be further configured to provide electrokinetic propulsion, pressure driven, or pressure directed flow of said plurality of molecules in said at least two defined directions. The device can be further configured to provide electrokinetic propulsion, pressure driven flow, or directed flow of said plurality of molecules in at least four defined directions. The device can further comprise a junction, wherein said junction connects two or more, or three or more microfluidic pathways.

The device can be configured for sensing molecular properties, wherein said molecular properties are selected from the group consisting of charge, optical absorbance, fluorescence, polarization, molecular size, molecular weight, molecular length, aspect ratio, magnetic moment, electric dipole moment, refractive index, electrical conductance, and capacitance. In some embodiments, the molecular properties are fluorescence. The molecular properties can be fluorescence at a first excitation wavelength and a first emission wavelength, and fluorescence at a second excitation wavelength and a second emission wavelength. The plurality of molecular properties can comprises fluorescence, wherein said fluorescence comprises at least two different emission wavelengths.

In some embodiments, the device comprises at least one laser. The device can comprise two lasers. The device can also comprise one or more of an excitation filter, a neutral density filter, a dichroic mirror, a fluorescence emission filter, and a photon detector. The dichroic mirror can comprise a single band dichroic mirror. The device can comprise an optical fiber. The device can comprise a photodetector. The photodetector can be a photomultiplier tube or an avalanche photodiode. The device can comprise an objective or a lens. The objective or lens can be a high numerical aperture objective or lens. In some embodiments, the device is configured to provide a low autofluorescence background.

In an embodiment, the device further comprises one or more of two excitation filters, two neutral density filters, two fluorescence emission filters, two dichroic mirrors, and two photon detectors. In another embodiment, the device can comprise two photon detectors that are selected from a photomultiplier tube and an avalanche photodiode.

The present invention provides for a device where one of two dichroic mirrors comprises a single band dichroic mirror, and one of the two dichroic mirrors comprises a dual band dichroic mirror.

The device can further comprise an electrically activated switching apparatus. The electrically activated switching apparatus can be configured to alter the direction of movement of said plurality of molecules from one defined direction to another defined direction. The electrically activated switching apparatus can be configured to electrokinetically alter the direction of movement of at least one of said plurality of molecules from one defined direction to another defined direction. The electrically activated switching apparatus can be activated by the simultaneous detection of a plurality of molecular properties of said plurality of molecules.

In some embodiments, the device can further comprise a computer.

In another embodiment, the present invention provides a device comprising: a fluidic inlet port, at least one fluidic outlet port, wherein said device is configured to provide a variable voltage potential between the fluidic inlet port and the at least one fluidic outlet port, a submicrometer channel comprising one or more junctions, an illumination source, and a photodetector; wherein said device is configured to optically interrogate a plurality of one or more molecular properties of a plurality of molecules disposed within and electrokinetically propelled or pressure driven through said submicrometer channel with single molecule resolution.

The photodetector can comprise one or more photomultiplier tubes or avalanche photodiodes. The illumination source can comprise one or more lasers. The molecular properties can be selected from one or more of charge, optical absorbance, fluorescence, polarization, molecular size, molecular weight, molecular length, aspect ratio, magnetic moment, dipole moment, refractive index, conductance, and capacitance. The device can further comprises a logic device, wherein said logic device is configured to detect time coincidence of two or more molecular properties of said plurality of molecules disposed within and electrokinetically propelled or pressure driven through said submicrometer channel with single molecule resolution. The device can further comprise a sorting trigger, wherein said sorting trigger is configured to sort said plurality of molecules disposed within and electrokinetically propelled through said submicrometer channel with single molecule resolution. The sorting trigger can be activated by a time coincident detection of two or more molecular properties of said plurality of molecules disposed within said submicrometer channel with single molecule resolution. The sorting trigger can be provided by the time coincident detection of two or more molecular properties of said plurality of molecules disposed within said submicrometer channel with single molecule resolution. The device can be configured to provide time coincident detection.

In any one of the foregoing embodiments, the device further comprises a high voltage sorting actuation circuit, wherein said high voltage sorting actuation circuit is configured to vary the voltage potential between the fluidic inlet port, and at least one of the at least one fluidic outlet ports. The high voltage sorting actuation circuit can be configured to vary the voltage potential between the fluidic inlet port and at least one of the at least one fluidic outlet ports in response to a signal from the sorting trigger.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 10A: depicts an array of 27 fluidic channel arrays on a fused silica.

FIG. 10B: depicts a zoomed in image of a fluidic channel.

FIG. 10C: depicts an exemplary setup involving a laser-induced fluorescence detection of single molecules within the cross-section of a nanofluidic channel.

FIG. 10D: depicts an exemplary analytical output of fluorescence data. The data is a 0.25 second time SCAN that illustrates the bound state native chromatin fragments in a nanofluidic channel using time-coincident detection events of green-labeled histone proteins to red-labeled DNA.

FIG. 11A: depicts a bifurcated nanofluidic channel.

FIG. 11B: depicts an image of a the bifurcated channel showing molecules that enter the top and are actively sorted to the left. Molecules satisfying a sorting condition are identified by the FPGA and shuttled to the correct branch. A compact, time-resolved record of events is also stored.

FIG. 11C: depicts a schematic showing the bifurcated channel, detector, field programmable gate array (FPGA), data recorder and computer, and the high-voltage sorting actuation circuit, and electrical connections.

FIG. 12A: shows a table showing collection efficiency using the experimental parameters given. Molecules were shuttled through a single branch, collected using a pipette and then quantified using qPCR to demonstrate a molecule collection efficiency ~25%.

FIG. 18: shows exemplary equations and calculations to determine the electrical properties of a bifurcated network.

FIG. 19: shows an illustrative overlay of a parallel network of external resistors.

DETAILED DESCRIPTION OF THE INVENTION

Figure 1:
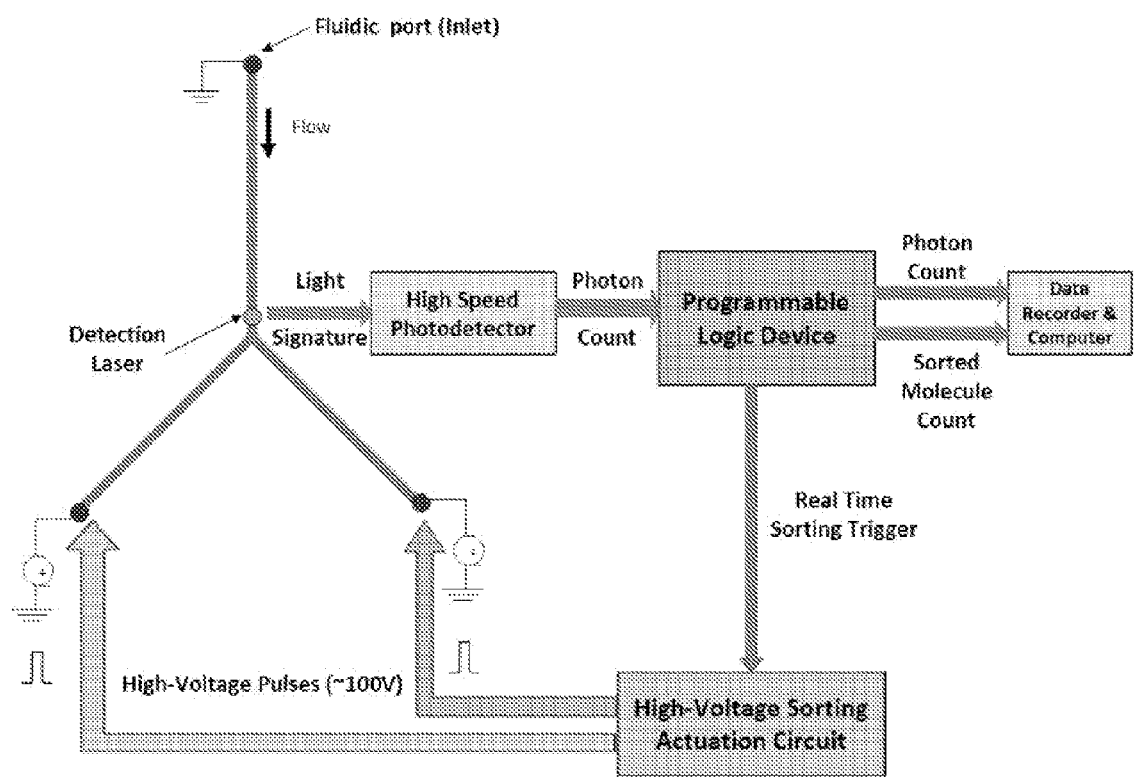
FIG. 1: depicts a block diagram of the fluidic channel, optical and electrical components of an exemplary sorting device of the present invention. An inexpensive programmable logic device is used to evaluate the light signature and provide a voltage signal or 'trigger' to actuate sorting. The trigger signal is converted to a high voltage signal, which then redirects a molecule's direction of molecular motion in the fluid channel.
Figure 2:
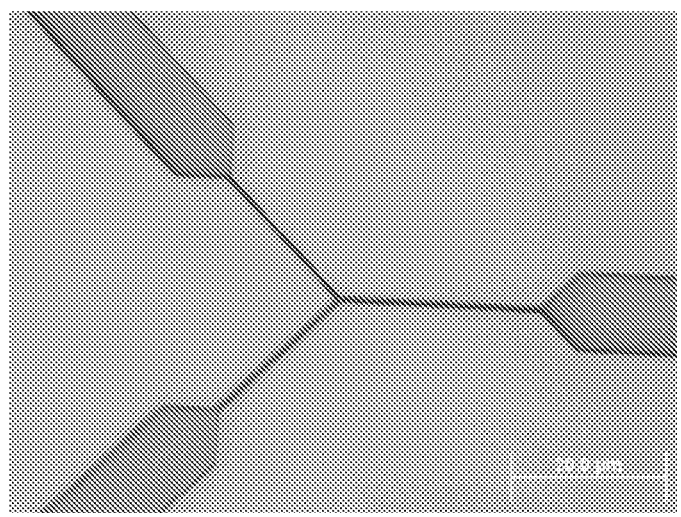
FIG. 2: is an optical micrograph of fluid channels used for sorting. This branched channel was etched in a polished fused quartz substrate and a lid was bonded to seal the channels. The narrow region of submicrometer width allows for the isolation and sorting of a single molecule in solution of relatively high concentration.
Figure 3:
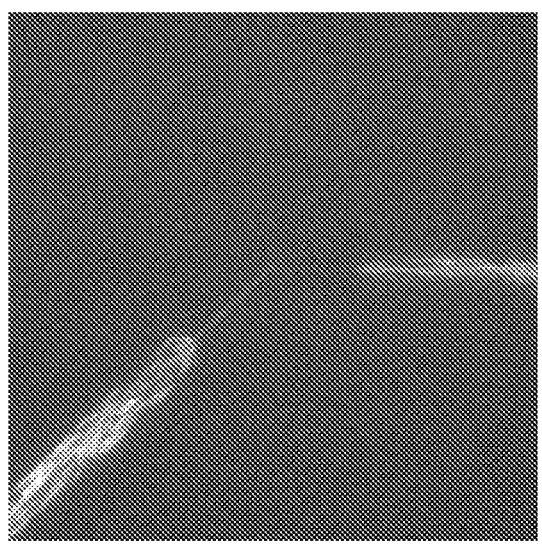
FIG. 3: is a fluorescence image of a fluidic channel with a directed flow of DNA. Directed flow of DNA molecules through the device is achieved by switching the applied voltage between the branches of the Y-shaped junction. Time-lapsed imaging is used to illustrate the high rate of molecule transit through the junction, exceeding 1000 molecules per minute.
Figure 4:
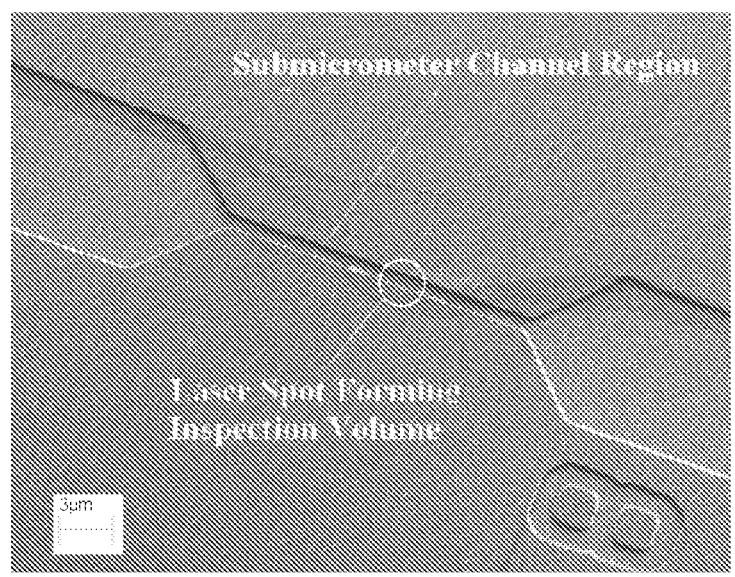
FIG. 4: is a micrograph of one microfluidic channel imaged by a scanning electron microscope. The channel is approximately 500 nm in width and height. A red circle is overlaid to indicate the approximate area illuminated by the focused laser spot.
Figure 5:
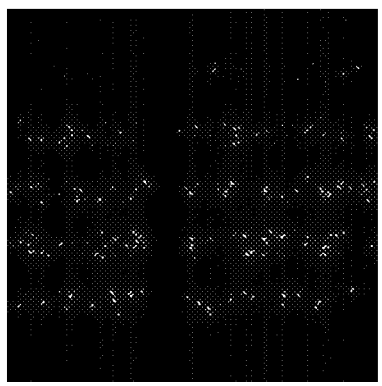
FIG. 5: illustrates fluorescence optical micrographs using field illumination to aid in visualization of DNA flowing through parallel networks of fluid channels. The figure of the left is a micrograph showing a snapshot of fluorescently-labeled DNA resting inside fluid channels. The figure on the right is a micrograph (with time lapse) showing the same fluorescently labeled DNA during the flow and single molecule isolation (constricted region).
Figure 5:
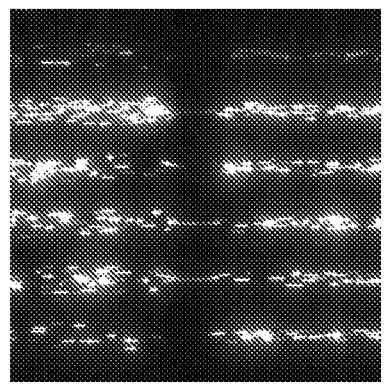
Figure 6:
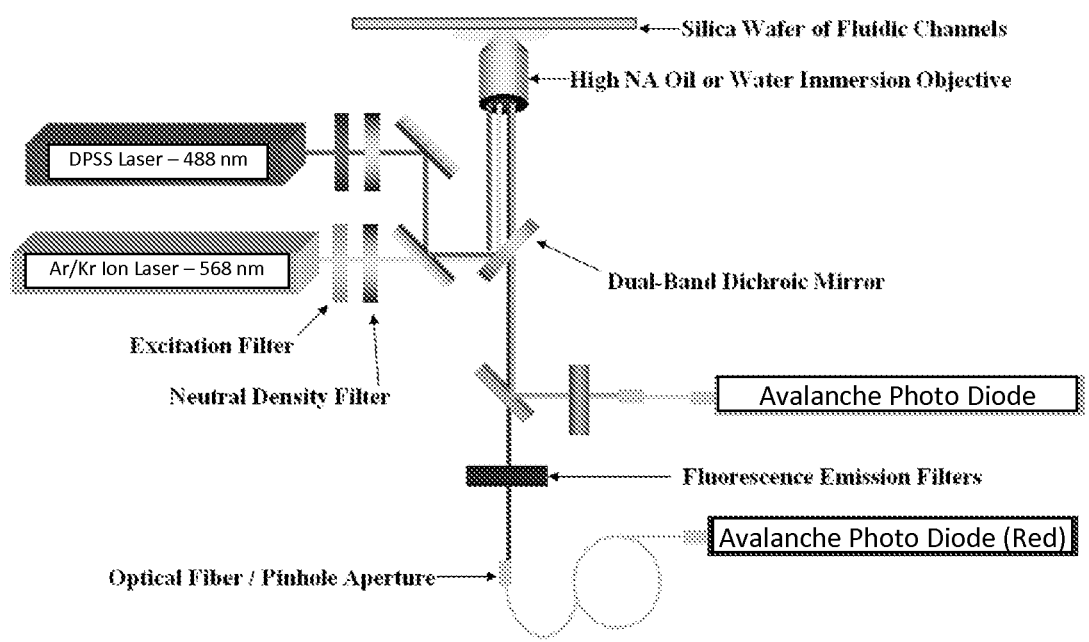
FIG. 6: depicts a schematic view of an exemplary sorting device of the present invention. The device has a two-laser induced fluorescence detection module.

The present invention provides systems, devices, and methods for automated sorting of selected molecules and/or objects. The subject invention typically utilizes a fluidic system to sort the molecules based on identifiable signals. Such identifiable signals include, but are not limited to, electrical, spectral, optical, fluorescence, electrical conductance, polarization, size, aspect ratio, refractive index, magnetic moment, and electric dipole moment. A device of the present invention can sort individual molecules from a collection, based on for example detection of fluorescent labels. The methods and devices herein have wide utility for sorting and analyzing molecules identified by their ability to bind a given label specifically or other detectable characteristics.

The devices and methods provided herein are also useful for other applications for identifying nucleic acid molecules that have affinity for a target molecule. Additionally the devices and methods provided herein may be useful for identifying bound components of a chemical library used for screening, such as drug screening. For example, the devices and methods provided herein may be useful for identifying nucleic acids, aptamers, small organic molecules or proteins bound to a target such as a therapeutic target (e.g. an enzyme, kinase, protease, protein, growth factor, carbohydrate etc.). This may allow, for example, a new more efficient ways of selecting potential drugs such as aptamer molecules which selectively bind the therapeutic target, binding agents such as proteins or antibodies which selectively bind the therapeutic target, or small organic molecules or for extracting a specific molecule or particle from a complex mixture for further analysis.

The systems, devices, and methods are particularly useful for analyzing and/or sorting objects. The term "objects" can refer to any molecule, single molecule, complex, cell, cellular component, or bead described herein. For example, the systems, devices, and methods may be used to sort biomolecules including but not limited to genetic material, nucleic acids (e.g. DNA, RNA, and hybrids thereof), nucleic acid fragments, proteins, protein fragments, aptamers, carbohydrates, lipids, nucleic acid-protein complexes, protein-protein complexes, and any combination thereof. The object can also be a cell, cellular component, or cell fragment. For example, the systems, devices, and methods may be used to sort other molecules, including polymers, organic molecules, small organic molecules, drugs, drug targets, and compounds. The sorter may also sort particles, such as beads, vesicles, and lipid vesicles. In some cases, the systems, devices, and methods provided herein may be utilized to sort nucleic acids that have specific bound proteins or altered chemical states for epigenetic analysis. In some cases, the invention provides for sorting of chromatin, which encompasses whole chromatin and chromatin fragments, and/or histones. The object to be sorted can be of a variety of sizes. For example, the object to be sorted typically has a dimension that is less than the size, diameter, or width of a channel in the sorting system. In some embodiments, all dimensions of the object are less than the width and height of the channel. In other embodiments, the length of the object may be greater than the width of the channel, e.g., an elongated nucleic acid. As described herein, the objects to be sorted can be measured for intrinsic properties, or may be labeled with another molecule that complexes with the object. Examples of such labels include fluorescent dyes, e.g., a quantum dot that is optionally conjugated to a nucleic acid probe. Other labels that can be utilized include intercalating dyes, e.g., YOYO-1, TOTO-3, Syber Green, and ethidium bromide.

The object or genetic material in the sample can be complexed, pretreated, or mixed with one or more labels. In one embodiment, the genetic material is labeled with a plurality of labels, at least one of which is specifically complexed with an epigenetic marker on said genetic material and at least one other label that is complexed with a protein and/or nucleotide of said genetic material. Labels include fluorescent dyes, quantum dots, magnetic particles, metallic particles, and colored dyes. Examples of dyes are described herein. The dyes or labels can be conjugated to binding moieties such as antibodies, nucleic acids, proteins, aptamers, affinity clamps, peptides, naturally occurring proteins and protein domains that bind to target proteins of interest. The binding moieties can be specific or generic. In some embodiments, one binding moiety is specific to an epigenetic marker and a second binding moiety generically binds to nucleic acids, proteins, or biological molecules.

Sorted objects can then be collected, sorted again, and/or further analyzed. For example, sorted nucleic acid molecules may be recovered and have their sequences or chemical signatures further analyzed using, for example, DNA sequencing, mass spectrometry, ELISA, immunoprecipitation, hybridization techniques (e.g. microarray hybridization) or PCR.

Devices

The present invention provides for systems and devices for sorting objects. A subject system typically comprises the following components: a channel that is fluidically connected to a plurality of downstream flow paths, said channel being adapted to hold said object in a continuous liquid body in said channel, one or more light sources configured to illuminate the channel to create one or more interrogation volumes, a detection module configured to detect at least two types of signals indicative of two distinct properties of the object in the one or more interrogation volumes, and a sorting module configured to direct the object to one of the plurality of downstream flow paths based on said two types of signals.

An exemplary setup is depicted in FIG. 1. For example, the sorting system can include a fluidic port or inlet that leads to a channel connected at a branch point to a plurality of downstream flow paths or channels. The downstream flow paths or channels can lead to additional fluidic ports or outlets. One or more detection regions can be positioned upstream and/or downstream to the branch point. The detection system may utilize a variety of detection techniques known in the art. In some embodiments of the invention, the detection system can utilize detectors that measure optical, electrical, radioactive, acoustical, physical (e.g., size, density, thermal conductivity, elasticity, viscosity, and strength), and/or magnetic properties. Optical properties can include luminescence, fluorescence, color, absorption, reflectance, resonance, and light scattering. Each of these optical properties can be measured at varying or distinct wavelengths or spectrums. Electrical properties can include conductance, resistance, electrical dipole, charge, impedance, or capacitance. The electrical properties can also be measured in a frequency domain. A detector can be configured to measure signals within an interrogation volume. The detector can transmit the measured signal to a programmable logic device, which can interpret and/or analyze the signal. The programmable logic device can provide instructions to a sorting actuation circuit, as shown in FIG. 1, so that the object can be sorted appropriately. The programmable logic device can also report the photon count and information regarding the sorting of the object to a data recorder and/or computer.

Figure 8:
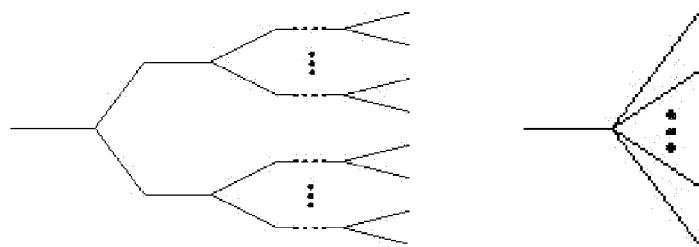
FIG. 8: depicts an embodiment of the present invention which provides increased sorting capability by incorporating additional branch points in series (left), or in parallel (right).
Figure 9:
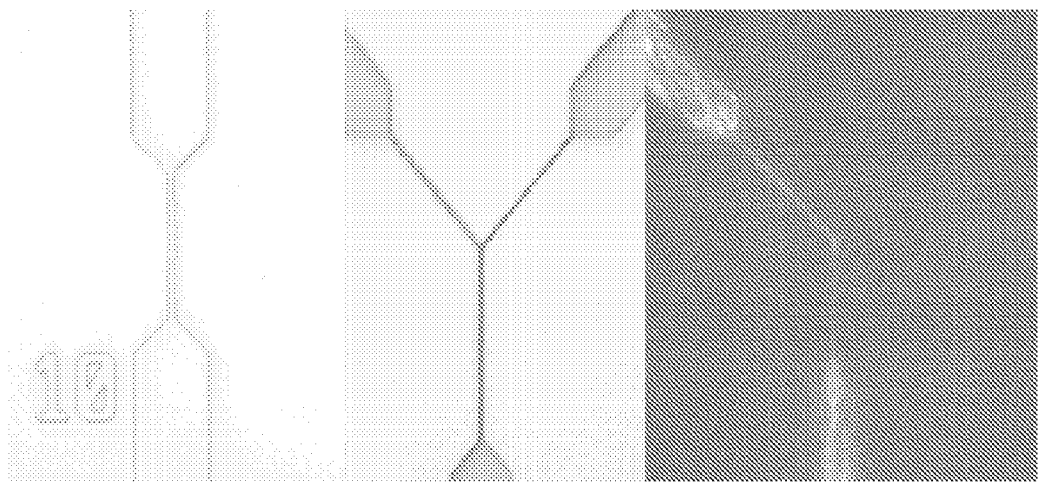
FIG. 9: depicts micrographs of an illustrative analytical and preparative device of the present invention. The figure on the left is a light micrograph of an analytical device of the present invention, in which the voltage gradient can be set up to run chromatin from bottom to top or from top to bottom. Middle, light micrograph of a sorting device in which the molecules are flowed from bottom to top, with the top two bifurcations representing the two possible outflow tracts. Right, long exposure fluorescent micrograph of TOTO-3 labeled DNA flowing through a sorting device from bottom to top. In this image, the electrode in the left arm of the outflow tract is charged, directing DNA to the left collection chamber. Note that the electrode in the right arm can be charged by the high-speed switch that is programmed to respond to observations made in the inspection volume, just below the bifurcation.

The sorted object may be detected and/or analyzed in the downstream flow path, or detected and/or analyzed after collection. Detection and analysis in the downstream flow path can be used to verify proper sorting, or to provide information on how to further sort and direct the object to one of a plurality of secondary downstream flow paths. FIG. 8 (left) depicts an arrangement of channels that includes a plurality of branch points or bifurcations that can allow for repeated sorting of an object. The detection and analysis in the downstream flow path can be similar to the detection and analysis performed in the upstream channel described above. The detection technique can be the same or different, and the same or different properties of the object can be measured. The detector in the downstream flow path can transmit a detected signal to the same programmable logic device, or a different programmable logic device. Instructions from a programmable logic device can be transmitted to the same sorting actuation device which can control the sorting of the object at any or all branch points, or can be transmitted to a different sorting actuation device which can control the sorting of the object at a branch point that is downstream and/or adjacent to the detector.

The sorting of the object can be repeated to create a 1, 2, 3, 4, 5, 6, 7, 8, or more sorting events. The repeated sorting can be performed using primary, secondary, tertiary, quaternary, quinary, senary, septenary, octonary, or more channels, detection regions, branch points, and downstream flow paths.

Channels

As noted above, the sorting devices can comprise one or more channels or flow paths. The channels can be fabricated using a variety of techniques, including microfabrication and nanofabrication techniques. The channels can be made from a variety of substrates, including, but not limited to, silica, mirror polished fused silica, silicon, quartz, glass, or polymeric materials (e.g., PDMS, plastics.). Channels may be etched, ablated, molded, into the substrate. The channels or flow paths may be coated. The coating can alter the properties of the channels and may be patterned. For example, the coating may be hydrophobic, hydrophilic, magnetic, paramagnetic, conductive, or be functionalizable depending on the objects to be sorted. The coating or a material complexed, conjugated, or bonded to the coating may exhibit affinity to one or more types of objects. The coating, or a material bound to the coating may reduce the adherence of an object to the channel. An example of a coating material includes PTFE. The channels may have a cross-section that is shaped like a circle, oval, rectangle, square, trapezoid, triangle, pentagon, or any other shape. The channel may have one or more cross-sectional dimensions, e.g., diameter, width and/or height, that is up to about, less than about, or about 10, 20, 30, 40, 60, 80, 100, 200, 250, 400, 500, 550, 600, 700, 800, 900, 1000, 1250, 1500, or 3000 nanometers. The dimension of the channel can be selected to be up to about, more than about, or less than about 1, 2, 3, 4, 5, 6, 7, 8, 9, 10, 15, 20, 25, 50, 75, or 100 times the width of an object to be sorted.

The one or more channels can be fluidically connected to one another at one or more branch points. The one or more channels allow for the sorting of objects in a continuous body of liquid or in a reversible fashion (as described herein). The branch points may be bifurcations, where a single upstream channel is connected to two downstream flow paths or channels at a bifurcation point. As shown in FIG. 8 (left) a sorting device can have a plurality of bifurcation points. In other embodiments of the invention, one or more channels can be fluidically connected at a branch point to more than two downstream flow paths or channels. As shown in FIG. 8 (right) a sorting device can comprise an upstream channel fluidically connected at a branch point to four downstream flow paths or channels. In some embodiments of the invention, a device has a plurality of branch points, each branch point having two, three, four, five, or more downstream flow paths or channels. The branch points may have the same or different number of downstream flow paths. The branch points may be T-shaped, Y-shaped, or any variation thereof. The channels may be straight or curved. The channels can be positioned in two or three dimensions, such that all channels are in the same plane, or some channels are in different planes.

The channels, including downstream flow paths and channels, may have the same of different dimensions. Downstream flow paths or channels may have the same, higher, or lower cross-section area as compared to an upstream channel. The dimensions of the channels can be selected to maintain fluid velocity within the channels. In one example, an upstream channel is fluidically connected at a bifurcation point to two downstream channels and the cross sectional area of each of the downstream channels is half the cross-sectional area of the upstream channel.

In some embodiments of the invention, a channel can be etched from a fused silica wafer to create a stack with 27 fluidic channel arrays, as shown in FIG. 10A. A fluidic channel can have a width of 500 nm and a depth of 250 nm, as shown in FIG. 10B. The channels may be microfluidic or nanofluidic channels.

Other examples of channels and sorting systems can be found in U.S. Patent Application Nos. 2009/0050542, and 2009/0234202, U.S. Pat. Nos. 6,927,065, 7,405,434 and 6,833,242, and PCT Publication No. WO/2010/044932 which are each incorporated herein by reference in their entirety.

Fluid carrying the object or the object alone can be directed through the channels using an external pressure source, an internal pressure source, electrokinetics, magnetics, or some combination thereof. The external or internal pressure source can be a pump, e.g., a peristaltic pump, syringe pump, or a pneumatic valve pump.

Electrokinetic forces can be applied to the object or a fluid carrying the object through the use of electrodes that are placed in electrical communication with the channels. Electro-osmotic and pressure-driven flow are examples of methods or systems for flow control, that is, manipulating the flow of molecules cells, particles or reagents in one or more directions and/or into one or more channels of the invention. Other methods may also be used, for example, electrophoresis and dielectrophoresis. In certain embodiments of the invention, the flow moves in one "forward" direction, e.g. from the inlet region through the main and branch channels to an outlet region. In other embodiments, the direction of flow is reversible. Application of these techniques according to the invention provides more rapid and accurate devices and methods for sorting, in part, because the sorting occurs at or in a branch point that can be placed at or immediately after a detection region. This provides a shorter distance for molecules or cells to travel, they can move more rapidly and with less turbulence, and can more readily be moved, examined, and sorted in single file, i.e., one at a time. In another embodiment, potential sorting errors can be avoided, for example by reversing and slowing the flow to re-read or resort a molecule or cell (or a plurality thereof) before irretrievably committing the molecule or cell to the outlet or to a particular branch channel.

Without being bound by any theory, electro-osmosis is believed to produce motion in a stream containing ions, e.g. a liquid such as a buffer, by application of a voltage differential or charge gradient between two or more electrodes. Neutral (uncharged) molecules or cells can be carried by the stream. Electro-osmosis is particularly suitable for rapidly changing the course, direction or speed of flow. Electrophoresis is believed to produce movement of charged objects in a fluid toward one or more electrodes of opposite charge, and away from one on or more electrodes of like charge. Because of its charged nature (2 charges for each base pair) DNA can be conveniently moved by electrophoresis in a buffer of appropriate pH.

Without being bound by any theory, dielectrophoresis is believed to produce movement of dielectric objects, which have no net charge, but have regions that are positively or negatively charged in relation to each other. Alternating, non-homogeneous electric fields in the presence of particles, such as molecules, cells or beads, cause them to become electrically polarized and thus to experience dielectrophoretic forces. Depending on the dielectric polarizability of the particles and the suspending medium, dielectric particles can move either toward the regions of high field strength or low field strength. For example, the polarizability of living cells depends on their composition, morphology, and phenotype and is highly dependent on the frequency of the applied electrical field. Thus, cells of different types and in different physiological states generally possess distinctly different dielectric properties, which may provide a basis for cell separation, e.g., by differential dielectrophoretic forces. See e.g., Fiedler et al. (S. Fiedler, et al. *Analytical Chemistry* 70, 1909-1915 (1998)).

Manipulation can also be dependent on permittivity (a dielectric property) of the particles with the suspending medium. Thus, polymer particles and living cells show negative dielectrophoresis at high-field frequencies in water. For example, dielectrophoretic forces experienced by a latex sphere in a 0.5 MV/m field (10V for a 20 micron electrode gap) in water are predicted to be about 0.2 piconewtons (pN) for a 3.4 micron latex sphere to 15 pN for a 15 micron latex sphere (Fiedler). These values are mostly greater than the hydrodynamic forces experienced by the sphere in a stream (about 0.3 pN for a 3.4 micron sphere and 1.5 pN for a 15 micron sphere). Therefore, manipulation of individual cells or particles can be accomplished in a streaming fluid, such as in a cell sorter device, using dielectrophoresis. Using conventional semiconductor technologies, electrodes can be microfabricated onto a substrate to control the force fields in a microfabricated sorting device of the invention. Dielectrophoresis is particularly suitable for moving objects that are electrical conductors. The use of AC current is preferred, to prevent permanent alignment of ions. Megahertz frequencies are suitable to provide a net alignment, attractive force, and motion over relatively long distances. E.g. Benecke (Benecke et al., U.S. Pat. No. 5,454,472 (1995)).

Figure 26:
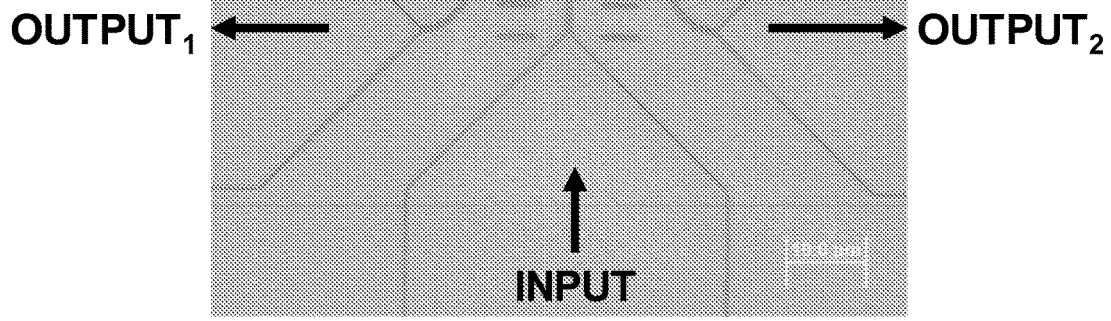
FIG. 26: shows an exemplary sorting device with arched channels.
Figure 28:
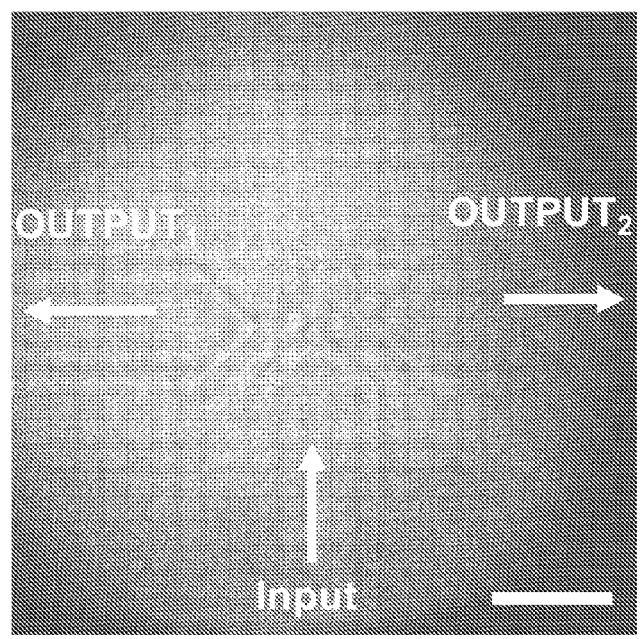
FIG. 28: shows a brightfield photomicrograph of an exemplary sorting device with arched channels. The scale bar is 40 micrometers.
Figures 29, 30:
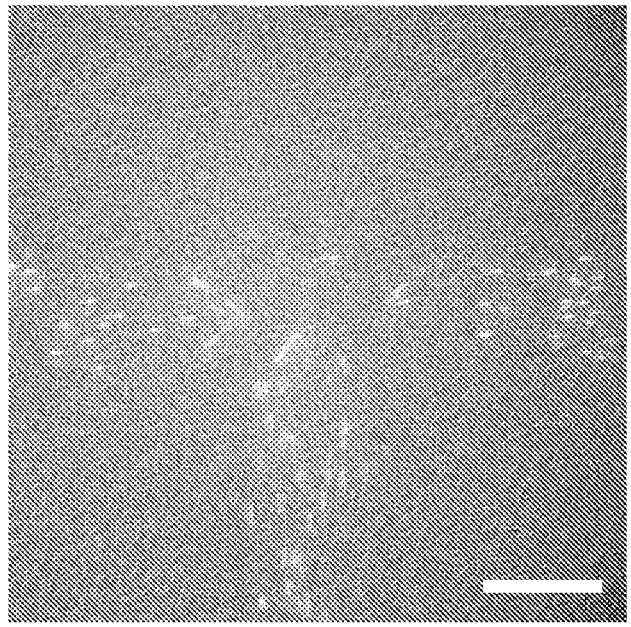
FIG. 29: shows a fluorescence photomicrograph of a solution containing 8 Kbp DNA intercalated with YOYO-1 flowing through arched channels and observed using widefield fluorescence microscopy.
FIG. 30: shows exemplary calculations and experimental measurements of channel resistive characteristics.

In some embodiments of the invention, the channels can be arranged such that channels that are upstream and downstream to a branch point have parallel portions. An exemplary embodiment is shown in FIG. 26. In FIG. 26, one input channel can leads to a branch point, and two output channels can be joined to the input channel at the branch point. The output channels can be arched such that a downstream portion of the output channels is parallel to the input channel. In other embodiments of the invention, the channels can be arranged such that one or more channels that are upstream and downstream to a branch point are within about, or less than about 1, 5, 10, 15, 20, 25, 30, 35, 40, 45, 50, 55, 60, 65, 70, or 75 microns of each other. These arrangements can allow for efficient setup, illumination, and detection of objects passing through the channels. FIG. 28 shows an exemplary brightfield image of such an arrangement. FIG. 29 shows a fluorescence image of an exemplary embodiment of a sorting system.

In FIG. 26, the inflow and outflow tracts can be 40 micrometers wide. Increase the width of the tracts can reduce the applied voltage necessary to achieve a specified molecule counting rate. In some embodiments, a 10 volt potential can be used to achieve a counting rate of 500-1000 molecules per minute, which can allow for the use of solid-state relays with ten times faster switching speeds, which can be on the order of an impulse response of the system.

Detection Module and Light Sources

The sorting system can comprise one or more detection modules configured to measure a signal corresponding to a property of the object to be sorted. The detection modules described herein can utilize a variety of detection techniques. The detection modules can detect optical, electrical, radioactive, physical (e.g., size, density, thermal conductivity, elasticity, viscosity, and strength), and/or magnetic properties. The detection modules can interrogate or inspect an object within a defined volume. The defined volume can be referred to as an interrogation volume, which is used interchangeably with the terms inspection volume and detection volume. In some embodiments, the interrogation volume is an optical volume wherein optical signals are detected. The interrogation volume is typically confined by the given wavelength of the light beam shining onto the channel and the properties of the wall of the shined channel. The detection modules can measure one, two, three, four, five, six, or more properties or signals from the object. For example, an object may have distinct measurable properties that change depending on the state of the object. These measurable properties can be intrinsic to the object, or can conferred by one or more labels that are complexed with the object. Examples of labels that can be complexed with the object include fluorescently labeled antibodies that complex with epigenetic markers on a nucleic-acid containing chromatin.

The choice of a detector can depend on the type of label used. For example, an optical detector can be used to detect a fluorescent label, and a conductance meter or electrical detector can be used to detect a metallic label. Examples of electrical detection systems are described in PCT Publication No. WO/2010/044932, which is hereby incorporated by reference in its entirety. An electrical detector can comprise a wire, a nanowire, a nanotube, a transistor, or a capacitor placed in proximity to a detection zone. The electrical detector can be made of carbon, silicon, carbon/silicon, or other semiconducting material.

A detection module utilizing optical detection of a property of the object can comprise a light detector or photodetector. The light detector can be a CCD, CMOS array, photomultiplier tube, avalanche photodiode (APD), single photon counting modules, photoreceptors, photovoltaic cells, phototransistors, LEDs, and any combinations thereof.

The detection module can include one, two, three, four, or more light sources. The light sources can include lasers, LEDs, fluorescent lamps, incandescent lamps, halogen lamps, gas-discharge lamps, and/or high-intensity discharge lamps. The one or more light sources can emit one or more beams of light that illuminate one or more regions or volumes within the one or more channels. The beam of light may be focused by an optical component, e.g., a high numerical aperture objective. The beams of light illuminating the channels can create one or more inspection volumes that are defined by the walls of a channel and the beams of light. The dimensions of the beam of light and the channel can define the size of the inspection volume, as shown in FIG. 10C. The inspection volumes can have a volume that is about, up to about, or greater than about 0.01, 0.05, 0.1, 0.2, 0.5, 0.75, 1, 5, 10, 25, 50, 75, or 100 femtoliters. The term inspection volume can also be referred to as an interrogation volume, optical volume, or a detection volume.

The light source can create a beam of light that is up to about, about, or greater than about 0.1, 1, 5, 10, 50, 100, 200, 280, 300, 500, 750, 1000, or 2000 µW within the interrogation volume.

In some embodiments, the plurality of light beams emit distinct spectrums or wavelengths of light into the same or different locations in the channel. The beams of light may create overlapping interrogation volumes or distinct interrogation volumes. The beams of light may have a diameter of about, less than about, or greater than about the width of the channel. In some embodiments, the beam of light is about, up to about, or greater than about 1, 1.5, 2, 3, 4, 5, 6, 7, 8, 9, or 10 times wider than the width of the channel. The width of the beam of light can be selected such that the light within the channel is substantially uniform.

The detection module can also include one or more optical components. For example, the detection module can include one or more high numerical aperture objectives or lenses, optical fibers, mirrors, dichroic mirrors, gratings, filters, and confocal apertures. The arrangement of the light source, detectors, and optical components can allow for detection of one, two, three, four, five, six, or more optical signals. The detection can be simultaneous or time-correlated. The resolution and/or accuracy of the time-correlation can be up to about or about 0.0001, 0.0005, 0.001, 0.005, 0.01, 0.05, 0.1, 0.5, 1, 5, 10, 50, 100, 500, or 1000 milliseconds.

Figure 27:
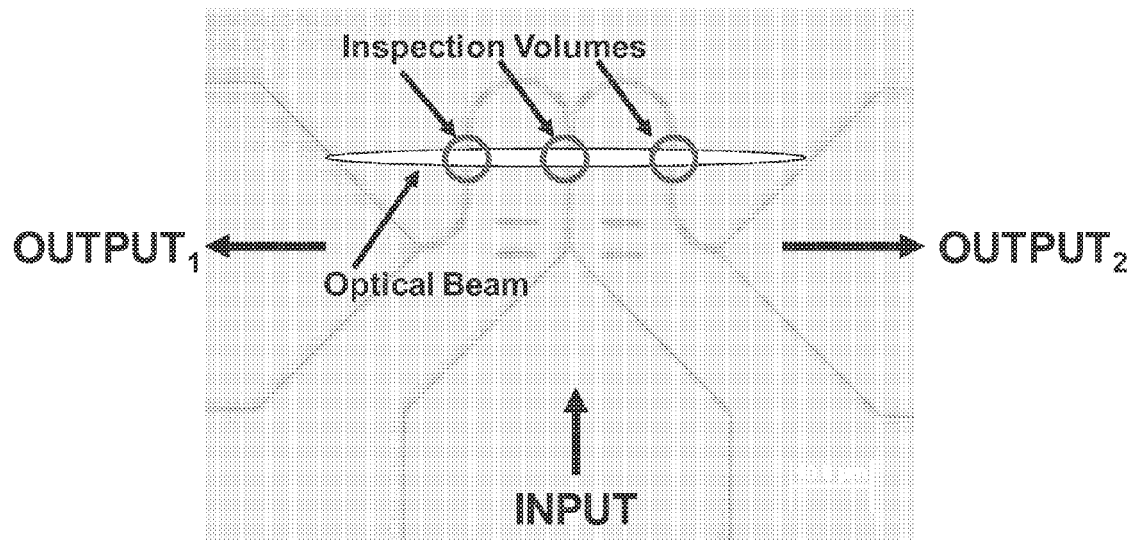
FIG. 27: shows an exemplary sorting device with arched channels and three inspection volumes. The inspection volumes are illuminated by a single optical beam.

The devices of the invention can be configured such that a plurality of inspection volumes can be illuminated by a single light source. As an example, FIG. 27 the device can comprise at least three inspection volumes that are positioned along a straight line. As an example, FIG. 27 shows a device comprising three parallel channels that are illuminated by a single beam of light. The single beam of light can be altered by an elliptical lens to create an elliptical beam of light. Objects passing through the three inspection volumes can then be measured by one, two, three, four, or more detectors. In some embodiments, each inspection volume is measured by a single detector. In some embodiments, two or more inspection volumes are illuminated by a single beam of light, and each inspection volume is monitored by a single detector.

The device, as shown in FIG. 27, can have w-shaped or arch-shaped channels. This can allow for simultaneous or time-correlated detection of the input and output. This can provide in situ verification of sorting performance and can provide the ability to reverse the flow and correct cases where improper sorting occurs. In some embodiments, such channels that allow for simultaneous or time-correlated detection can have oblique or acute angle bifurcations, serpentine-shaped channels with multiple branching points, and circularly symmetric input channels. Circularly symmetric input channels can facilitate a Cd-player type readout of the inspection volume.

The arrangement of a plurality of inspection volumes, e.g., two, three, four, or more inspection volumes, along a common axis and/or maintaining a small distance between each inspection volume can reduce beam-to-channel alignment time and tolerances in a free-space optical setup. The compact structure can reduce sensitivity to misalignments in rotation and mechanical drift of the fluidic device relative to the confocal inspection volumes (or optical setup) in either the x or y (in-plane) directions. This can allow for improved alignment stability, reduction in systematic variations in signal-to-noise, and longer duration experiments. The devices of the invention can be arranged such that stable measurements can be taken over the course of about, or more than about 1, 5, 10, 15, 25, 30, 35, 50, 60, 90, 180, 270, 360, 480, or 960 minutes.

In some embodiments of the invention, a light source and/or detector can be integrated with the fluidic device. The integrated light source and detector can include an integrated wave guide, LED, laser diode, or plasmonic focusing bow-tie. In other embodiments, the detection is electrical and can include integrated electrodes that can be located within or near the backplane of the fluidic channel.

The one or more detectors can be configured to transmit information regarding the one or more detected signals to a processor. The processor can be a programmable logic device, a computer, or any other component that can record or interpret the signal. The processor may be a component of a sorting module, described herein.

As shown in FIG. 1, a detection laser, can be positioned just upstream to the branch point. The detection laser can illuminate the channel to create an inspection volume.

As shown in FIG. 1, a high speed photodetector can detect light emitted from the interrogation zone and convert light into a photon count. The photon count can be transmitted to a programmable logic device. The programmable logic device can interpret the photon counts and determine how the object is to be sorted based on the photon counts.

Sorting Module

The sorting system can comprise a sorting module that interprets one or more signals measured by the detection module and/or directs an object to one of a plurality of downstream channels or flow paths. The information transmitted by the detection module or the detector can be received by a processor. The processor can be a computer or a programmable logic device, e.g., a field-programmable gate array (FPGA), PAL, GAL, or CPLD. The processor can operate at about, up to about, or greater than about 15, 25, 50, 60, 75, 100, 200, 500, 1000, or 2000 Hz, MHz, or GHz. In some embodiments, the processor is an FPGA that can interpret data and return instructions in less than about $1\times10^{-2}$, $2\times10^{-2}$ $1\times10^{-3}$, $1\times10^{-4}$, $1\times10^{-5}$, $1\times10^{-6}$, or $1\times10^{-7}$ seconds. The processor can be programmed to receive a measured signal and direct an object to one of a plurality of downstream flow paths. The conditions for sorting an object to one path or another can be programmed into the processor by a user via a user interface on a computer system or another device. The conditions for sorting an object can include simultaneous or time-correlated detection of two, three, four, five, six, or more signals. Detection of more one, two, three, four, five, six, or more signals above a preselected threshold can be used to discriminate objects. In some embodiments, the signals correspond to optical, electrical, magnetic, radioactive, or physical properties of the object. The signals measured can be indicative of distinct properties of the object.

The processor can interpret the data to determine how to sort the object and transmit instructions to a sorting actuator. The processor can interpret data obtained at one interrogation volume positioned in an upstream channel and provide instructions to a sorting actuator to direct the object to one of a plurality of downstream flow paths at one, two, three, four, five, or more branch points. The processor can interpret data obtained at one interrogation volume and return instructions to a sorting actuator to direct the object to one of a plurality of downstream flow paths at a branch point immediately adjacent and/or downstream to the interrogation volume. The branch point can be a known distance, volume or time away from the interrogation volume. Precise knowledge of the distance, volume, or time between the interrogation volume and the branch point can allow for accurate and/or precise sorting of the object. Reduction of the distance, volume, or time between the interrogation volume and the branch point can increase the precision and/or accuracy of sorting.

The sorting actuator can perform sorting of the object by changing the trajectory or flow path of the object. The sorting actuator can also change the trajectory or flow path of the object or of a fluid carrying the object. The sorting actuator can sort the object by physically altering the flow paths within the channels and downstream flow paths, or by imparting magnetic, electrical, or optical forces. In some embodiments, the sorting actuator can comprise one or more electrodes that impart an electrokinetic force on the object. Alternatively, the sorting actuator can comprise one or more valves that change the flow path of a fluid carrying the object. The valves can be pneumatic valves, mechanical vales, magnetic valves, rotary valves, hydraulic valves, piezoelectric valves, shuttle valves, elastomeric valves, and electrical valves. In some embodiments, electrodes can also be used to change the flow path of a fluid carrying the object. Electrostatics can also be used to alter the flow path of an object. Optical tweezers may also be used to alter the flow path of an object by placing the object in a position to flow down one of a plurality of downstream flow paths or deflecting the object toward one of a plurality of downstream flow paths. Optical tweezers can be used in the invention to trap and move objects, e.g. molecules or cells, with focused beams of light such as lasers.

A sorting system utilizing electrokinetic force is shown in FIG. 1. Each of the electrodes can be positioned within about, less than about, or greater than about 0.01, 0.5, 1, 2, 5, 10, 20, 50, 75, 100, 200, or 300 mm of a branch point. In some embodiments, the electrode is positioned outside of the interrogation volume and/or the switching volume. One set of electrodes may be used to direct the object down the channels, and a second set of electrodes may be used to selectively direct the object to one of a plurality of downstream flow paths. The second set of electrodes may be placed in closer proximity to the branch point, or may be positioned about only one branch point. Use of specific electrodes can allow for sorting of an object in systems utilizing a plurality of branch points placed in series.

Figure 23:
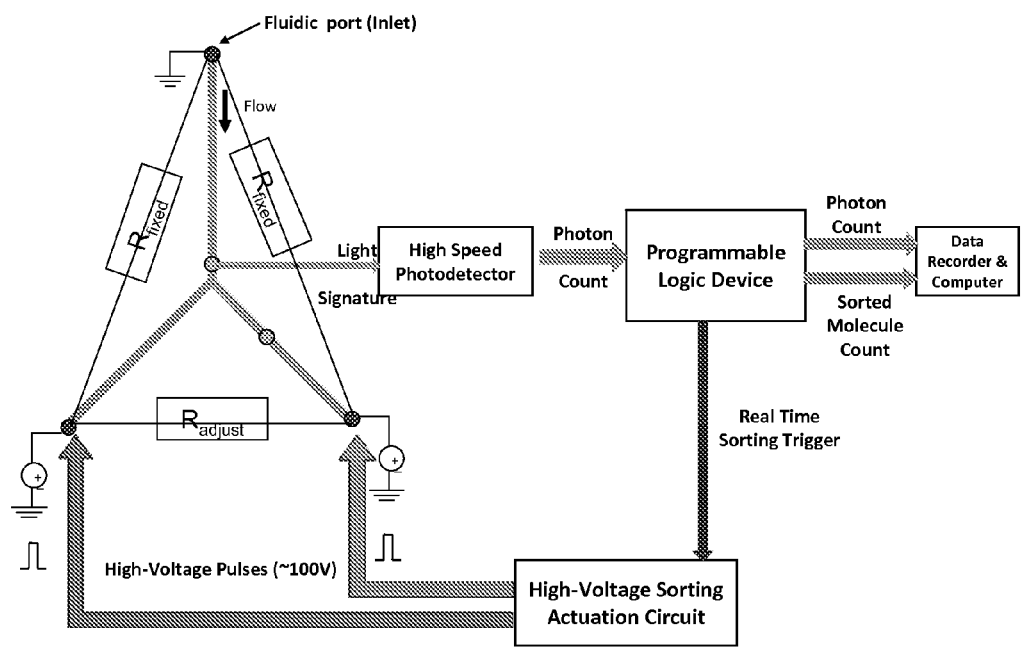
FIG. 23: shows a schematic of an exemplary molecular sorting hardware of the present invention. Fixed resistors and variable resistors are used to facilitate sorting. A detector and a programmable logic device are used for providing a real-time sorting trigger. The sorting hardware also includes a data recorder and computer, a high-voltage sorting actuation circuit, and electrical connections.

The sorting system can also include electrical connections between the electrodes in addition to the electrical connection provided by fluid within the channels. For example, external resistors may be placed between inlet and outlet ports of the fluidic channels, as shown in FIG. 23. The use of external resistors can allow for increased precision and accuracy in sorting the object. External resistors can also reduce the voltage required to sort the object.

Figure 25:
FIG. 25: shows a comparison of reed relays to solid state relays.
Figure 25:
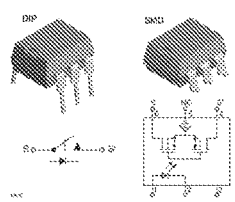

In some embodiments of the invention, the sorting module can include relays. The relays can be solid state relays and/or reed relays. Relays can be used to switch the voltage applied between one of a plurality of electrode pairs. As shown in FIG. 25, reed relays and solid state relays have relational advantages.

In some embodiments of the invention, a processor can include a smoothing function. The smoothing function can reduce noise and facilitate data interpretation. The smoothing function can be a summing or convolution filter. In some embodiments, the summing or convolution filter uses a window of about, less than about, or more than about 1, 2, 3, 4, 5, 6, 7, 8, 9, or 10 bins. A bin can be a time frame of about, less than about, or greater than about 1, 5, 10, 25, 50, 100, 150, 200, 250, 500, 750, or 1000 microseconds, milliseconds, or seconds. A summing filter can sum the signal that is within a window of 5 bins about a bin of interest. Other filters can sum the signal within a window of 5 bins about a bin of interest and divide by the number of bins.

The electronics of the sorting system can include an adjustable sorting actuation delay. The adjustable sorting actuation delay can facilitate sorting of an object by allowing a user to tune the time when sorting should occur without altering the position of the interrogation volume. This can be important for experimental setups involving optics and fluidics in static configurations. The delay can be programmed to be between a range. The range can be between 0 to 3, 6, 9, 10, 12, 12.8, 15, 18, or more milliseconds. The increments can be about, less than about, or greater than about 0.01, 0.1, 1, 5, 10, 20, 25, 50, 75, 100, 125, 150, 175, 200, 250, 500, 750, or 1000 microseconds.

Computer System

The sorting system can be operably linked to a computer that has a user interface for controlling sorting system (e.g., the detection module and the sorting module), programming the programmable logic device, and displaying results. The computer can be an integral part or a separate part of the subject sorting system. The user interface can be a graphical user interface. The user interface can display the measurements by the detector, the analysis of the object, and the sorting of the object, which may be in real-time. The user interface can allow for selection of operating conditions, e.g., voltage gradient, sorting conditions, signal thresholds, total sorting time, light source power, and detector calibration. The operating conditions can be inputted using a keyboard, mouse, or other input device.

In some embodiments of the invention, the sorting system comprises a memory module for storing data transmitted by the processor and/or detector during sorting. The memory module can be accessed during sorting or subsequent to sorting to retrieve data collected during sorting.

Methods

The invention provides for methods for sorting objects based on one or more properties of the object. The properties can be any of the properties described herein. The objects to be sorted are flown into a channel of the subject system. Upon measuring one or more properties of the object, the object is automatically selected and directed to one of a plurality of downstream flow paths based on the measured one or more properties. The sorting of the object can occur while the object is suspended in a continuous body of fluid that can be reversibly sorted. The measurement of the properties can be performed using a corresponding type of measurement described herein. For example, measurement of an optical property can be measured using an optical detection system and an electrical property can be measured using an electrical detection system. Examples of electrical detection systems are described in PCT Publication No. WO/2010/044932, which is hereby incorporated by reference in its entirety. Measurement of a property of the object can be performed within an interrogation volume. In some embodiments, the interrogation volume is created by illumination of the channel and defined by the dimensions of a beam of light and the walls of the channel. The sorting of the object can be based on one, two, three, four, five, six, or more distinct properties of the object. In some embodiments, the molecule can be sorted through a plurality of branch points placed in series, created by a plurality of interrogation volumes that are also placed in series. Accurate sorting of the molecule can also be verified using interrogation volume placed downstream to a branch point.

A sample containing the objects to be sorted and other materials can be delivered to an input reservoir of the sorting system. The concentration of the objects can be about, up to about, or greater than about 1, 5, 10, 20, 50, 100, 200, 30, 500, 750, or 1000 nanomolar, micromolar, or millimolar. In some embodiments, the sample can be diluted to a concentration such that the expectation of a molecule within the interrogation volume within a preselected period of time is 0.5, 1, 2, 5, or 10. The preselected period of time can be 0.001, 0.005, 0.01, 0.05, 0.1, 0.5, 1, 5, 10, 50, 100, 500 or 100 milliseconds.

The object in the sample can be complexed, pretreated, or mixed with one or more labels. Labels include fluorescent dyes, quantum dots, magnetic particles, metallic particles, and colored dyes. Examples of dyes are described herein. The dyes can be conjugated to a binding moieties such as antibodies, nucleic acids, proteins, or aptamers. The binding moieties can be specific or generic. In some embodiments, one binding moiety is specific to an epigenetic marker and a second binding moiety generically binds to nucleic acids, proteins, or biological molecules.

In some instances, two generic dyes and one specific dye corresponding to a first property can be used. This can allow for distinction between free dye, objects without the first property, and objects with the first property. In other embodiments, two generic dyes and two specific dyes may be used, where the first specific dye corresponds to a first property and the second specific dye corresponds to a second property. In addition to detecting free dye, objects without a first property, and objects with a first property, this would allow for detection of objects without either the first or second property, objects with the second specific property, objects without the second property, and objects with both the first and second property.

In some embodiments, the sample is processed by the sorting system without removal of free dye and/or free label. The free dye and/or free label can be sorted appropriately by the sorting system by use of time-correlated or simultaneous detection of a plurality of properties. In other embodiments of the invention, free dye and/or free label is removed from the sample prior to sorting. The concentration of the free dye and/or free label in the sample can be about, less than about, or greater than about 0.01, 0.05, 0.1, 0.2, 0.3, 0.4, 0.5, 0.6, 0.7, 0.8, 0.9, 1, 2, 3, 4, 5, 6, 7, 9, 10, 15, 30, 50 times the concentration of the dye and/or label that is complexed with the object.

Detection

In some embodiments, the present invention provides devices, which may be microfluidic or nanofluidic, useful for simultaneous or time-correlated detection of various molecular properties including, but not limited to, fluorescence, such as quantum dot fluorescence signatures. As described herein, the properties of the object can be measured using a variety of detection techniques. The detection modules can detect optical, electrical, radioactive, physical (e.g., size, density, thermal conductivity, elasticity, viscosity, and strength), and/or magnetic properties. In some cases, the present invention provides nanofluidic devices suitable for analytical purposes. The fluorescence signatures can be observed in real-time and in fact be used as triggering events to control a sorting method as provided herein.

Properties of the object can be detected in a simultaneous or time-correlated fashion. Simultaneous detection can occur by measuring two or more properties of the object at one instant in time. For example, two wavelengths of light corresponding to two distinct labels can be measured in a single interrogation volume, or overlapping interrogation volumes. Alternatively, two or more properties of the object can be measured at distinct times. This may be performed if the location of the object within the channel as it is travelling down the channel can be known, predicted, or estimated. For example, a first property can be measured at a first interrogation volume located upstream to a second interrogation volume, where a second property of the object is measured. Correlation of the signals from the first interrogation volume and the second interrogation volume can be based on the velocity of the object through the channel and the distance between the two channels. In this manner, 2, 3, 4, 5, 6, 7, 8, 9 or more properties of the object can be measured simultaneously or in a time-correlated fashion.

In other embodiments of the invention, the flow of the object can be reversed. This can allow for more than one measurement to be taken on an object within a single interrogation volume. Alternatively, multiple interrogation volumes can be placed in a channel prior to a branch point such that multiple measurements of the same properties are performed on the object prior to a sorting event. For example, two, three, four, five, six, seven, or more interrogation volumes may be positioned upstream to a branch point, thereby allowing for a plurality of measurements of the same two, three, four, five, or more properties used to determine how to sort the object.

Sorting

The detection and real-time evaluation of objects and/or collection of the objects can be carried out by the sorting module of the present invention. The sorting of the object can be based on one, two, three, four, five, or more properties measured during detection. The properties can be measured simultaneous, or in a time-correlated fashion. A processor can be used to interpret the data collected on the object and determine a desired flow path for the object.

The detection and real-time evaluation of spectral or other single molecule signatures and/or the separation and collection of these specific molecules can be carried out by the sorting module of the present invention. In some embodiments, the devices and methods of the present invention provide on-the-fly evaluation of both time and spectrally coincident signatures examined within the highly confined structures of the device (fluidic channels, nanopores, or otherwise). Single molecule separation using these coincident signatures may provide salient features, such as the ability to separate specific sequences of nucleic acids bound with proteins or separate molecules in the presence of other biological species or spurious fluorescence contamination, all with an extremely low rate of false-positive detection.

One example of such an implementation is to identify rare epigenetic modifications to histone proteins bound in chromatin. The device of the present invention provides unambiguous identification of the sequences moving through the channels and provides for selection of these molecules through separation, even in the presence of other cellular debris and proteins which often accompany the chromatin strands.

In some embodiments, objects can be analyzed, sorted, and verified one at a time in a device of the present invention. For example, one object can enter an upstream inspection volume, detected, sorted to one of a plurality of downstream channels, and then verified in a downstream channel prior to the entry of a subsequent object to the upstream inspection volume. In other embodiments, more than one object can be analyzed, sorted, and verified at a time. For example, a first object can enter an upstream inspection volume, and a second object can enter the same upstream inspection volume prior to the first object either being sorted or being verified. Analysis of a single object at a time can be termed synchronous detection and analysis of a plurality of objects at a time can be termed asynchronous detection. Asynchronous detection can increase the rate of sorting.

The object can be sorted by itself, or along with a fluid carrying the object, also referred to as a switching volume. In the case of a device utilizing valves to control the flow of a fluid carrying the object, the timing of the valves to selectively sort the object to one of a plurality of downstream flow paths can change the amount of fluid that is sorted along with the object. The switching volume can be the liquid sorted with the object as it is being sent through a branch point to a downstream flow path. The switching volume can be no greater than about 0.2, 1, 5, 7.5, 10, 25, 50, 75, 100, 200, 300, 500, 750, 1000, 2500, 5000, or 10000 femtoliters. The switching volume can be no greater than about 1, 10, 50, 100, 500, 1000, 5000, 10000, 50000 times the volume of the object. The switching volume can be no greater than about 1, 10, 50, 100, 500, 1000, 5000, 10000, 50000 times the volume of the interrogation volume. If the object is known to be within a volume of fluid that is about 100 femtoliters, then the switching volume may be 100 femtoliters. If the object is known to be within a volume of fluid that is about 10 femtoliters, then the switching volume may be 10 femtoliters. If the object is directed to one of a plurality of channels without moving the surrounding fluid, then the switching volume can be about or less than about 0, 0.001, 0.005, or 0.01 femtoliters.

In some embodiments of the invention, the sorting can increase the concentration of the object. The concentration can be increased by a magnitude of about or greater than about 1, 2, 3, 4, 5, 6, 7, 8, 9, 10, 11, 12, or more. The increased concentration of the object can be obtained by using low switching volumes. For example, if a sample contains 1000 objects to be sorted in a 1 mL solution and the switching volume is 100 femtoliters, the 100 objects to be sorted will be sorted with 100 femtoliters each. Therefore, the 100 objects will be collected in a reservoir with 10000 femtoliters, or $1 \times 10^{-8}$ mL, which corresponds to a concentration of 8 orders of magnitude.

Conventional sorting methods often involve valves and gates that move at the 10's of millisecond time scale or slower. However, the present invention provides high-throughput detection in excess of $2 \times 10^3$ molecules/min, $3 \times 10^3$ molecules/min, $5 \times 10^3$ molecules/min, $2 \times 10^4$ molecules/min, $5 \times 10^4$ molecules/min, $1 \times 10^6$ molecules/min, $2 \times 10^6$ molecules/min, $6 \times 10^6$ molecules/min, $7 \times 10^6$ molecules/min, $1 \times 10^7$ molecules/min or higher. Therefore, one advantage of the present invention is the ability to provide for high speed sorting of detected molecules or events. The present invention provides two high-speed methods of sorting to exert control over a molecule's trajectory, electrical and optical. These sorting methods can be implemented in nanofluidic and/or microfluidic channels using a branched or Y-shaped separation chamber for sorting. In some cases, devices of the present invention incorporate additional branch points, either in series or in parallel, further increasing the sorting capabilities if needed (FIG. 8).

In the present invention, a high-throughput counting in excess of 2,000 molecules/min has been demonstrated and this can be increased much further. Therefore, a high-speed sorting method is essential. At least two high-speed methods of sorting may be used to exert control over a molecule's trajectory, those being electrical and optical. These sorting methods may be implemented in nanofluidic channels using a branched (e.g. Y-shaped) separation chamber for sorting. Additional branch points may be incorporated, either in series or in parallel, further increasing the sorting capabilities if needed.

In one embodiment of the present invention molecules, such as nucleic acids, are electrokinetically driven through a Y-shaped channel that provides an opportunity to sort and collect specific molecules. The device and methods needed for molecular sorting are substantially different as required for rapid sensing and sorting of individual molecules. As shown herein, the present invention provides methods for fabrication and use of a device for flowing of chromatin through a sorting chamber that can be electrically activated. In some cases, coincident detection of two different fluorescent dyes may be used to identify the molecules of interest. In some cases, the methods of the present invention provide for labeling of molecules such as DNA with one dye or label and labeling of a specific protein, methylation state or other marker or modification of interest with another dye or label. In other cases, a therapeutic target is labeled with one label and a chemical library for drug screening containing small molecules, peptides, proteins, or aptamers (some of which can bind to the target) is labeled with another label. Coincident detection of the two different labels may be used to identify molecules from the chemical library that bind to the therapeutic target. Such molecules that are identified as binding to the target may then be identified as candidate therapeutics or candidate leads for therapeutic development.

Among these modifications useful for detection, sorting, and analyses by the devices and method of the present invention are DNA methylation and a variety of histone changes including tri-methylation of histone H3 lysine 27 (H3K27), which marks silent genes, and tri-methylation of histone H3 lysine 4 (H3K4) which marks active genes. DNA methylation is dramatically remodeled during development beginning with the pre-implantation mouse embryo. Little is known about how H3K27 and H3K4 methylation state change in the embryo, however, work with ES cells suggests that presence of both marks simultaneously on chromatin is a fundamental feature of stem cells, and as cells differentiate, one mark or the other is retained.

The invention provides nanofabricated devices that can sort individual DNA fragments over 50 kbp in size, visualize them under multi-color (e.g. 2, 3, 4, 5, 6, 7, 8, 9, 10 or more) fluorescence microscopy and collect data that reveals fluorescent signal intensities at approximately 100 bp resolution along the DNA strand. These methods may be utilized, for example, to characterize chromatin states in preimplantation mouse embryos. In some embodiments, chromatin may be isolated, labeled with fluorescent antibodies against RNA polymerase II, tri-methylated H3K27 and tri-methylated H3K4. Individual chromatin templates may then be analyzed for the presence and spatial location of these proteins using the methods and devices provided herein. The methods and the devices herein provide for determining the chromatin states across the genome and at genes poised to be transcribed in the pre-implantation mouse embryo, with unprecedented sensitivity and resolution.

Figure 31:
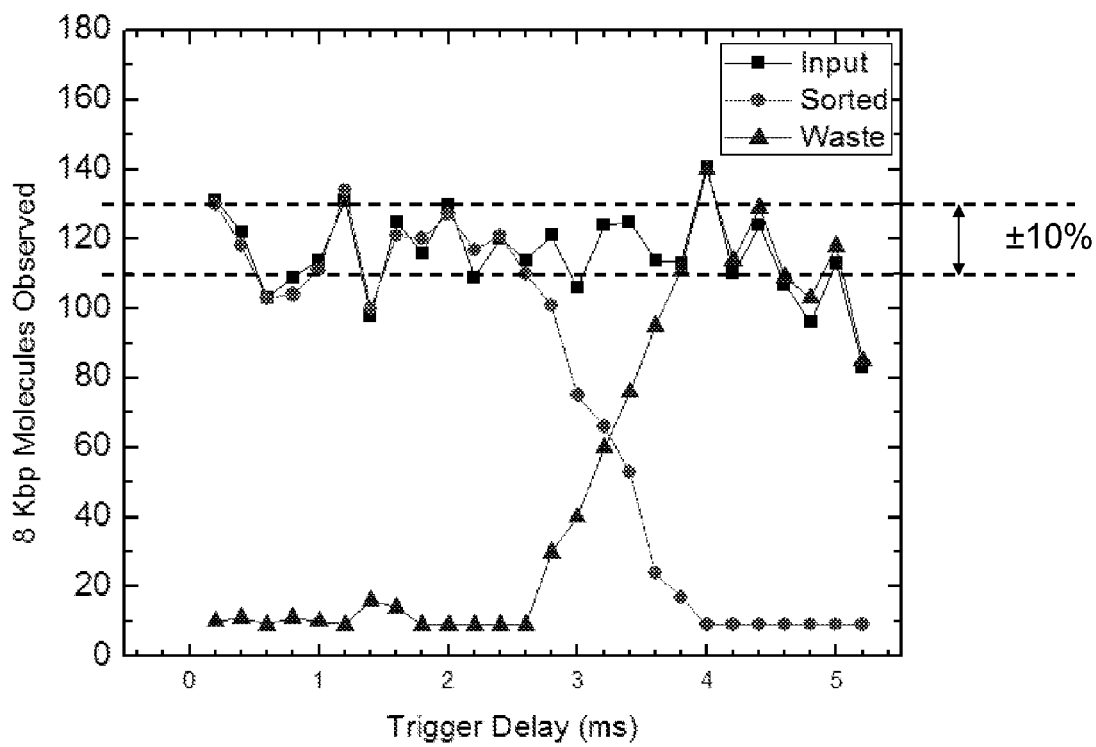
FIG. 31: shows a graph of 8 Kbp molecules observed as a function of trigger delay.

The methods of the invention provide for the tuning of an adjustable sorting actuation delay. An example of the response of changing an adjustable sorting actuation or trigger delay is shown in FIG. 31. In FIG. 31, a mixture of 2 and 8 Kbp fragments was delivered to an input channel. The sorting of the fragments was measured in a stable setup for about a 25 minute time period. The sorting threshold was 300 and the pulse width was 10 milliseconds. The point at which there is a transition in sorting (here around 3-4 ms) can be dependent on the bifurcation region and relay switch time.

In some embodiments, the accuracy of the sorting module can be measured based on a measure of objects sorted in each channel as compared to the objects entering the input channel. Objects sorted can be measured by downstream interrogation volumes and objects entering the input channel can be measured by an upstream interrogation volume. The upstream and downstream can be relative to a branch point connecting the input channel to two or more downstream channels. In some embodiments, the loss or gain in objects can be about, or less than about 0.01, 0.1, 0.5, 1, 2, 3 4, 5, 5, 6, 7, 9, or 10%

Electrical Sorting

In some embodiments of the present invention, electrical sorting is used to sort molecules based on detection of events or molecular properties. The present invention provides a device that can rapidly switch the voltage applied to a branched fluid channel to separate the molecules of interest into a collection volume. Appropriate design of the fluid system, electronic switching allows for rapidly interrogating large numbers of molecules in the sorting system.

Figure 7:
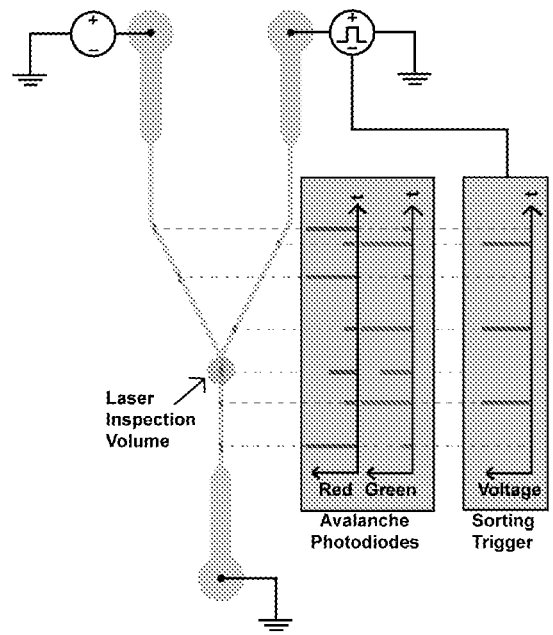
FIG. 7: illustrates schematic diagrams of two different embodiments of the present invention for sorting single DNA molecules. A. Electrical Method of Sorting: Fluorescently labeled chromatin flows from bottom to top and is identified in the laser inspection volume immediately before the Y-shaped separation chamber. Based upon the molecule's color signature, a sorting trigger controls the applied voltage. In this example, Chromatin exhibiting a predominantly green fluorescence is sorted to right of the Y-split. B. Optical Method of Sorting: Similar to FIG. 7A, fluorescently labeled molecules are identified in the laser inspection volume. Based upon the sorting trigger the particle trapping laser is deflected from the capture position (at the bottom of the Y-branch) into the left or right branch, directing the molecule as desired. In this example, Chromatin-quantum dot conjugates exhibiting a predominantly green fluorescence are sorted to right of the Y-split, while red fluorescent conjugates are sorted to the left. In some embodiments, the device of the present invention provides three-color detection (e.g. red, green, yellow), which can provide for sorting of chromatin with two colors into one branch (e.g. red and green) and two colors in the other branch (e.g. green and yellow).
Figure 7:
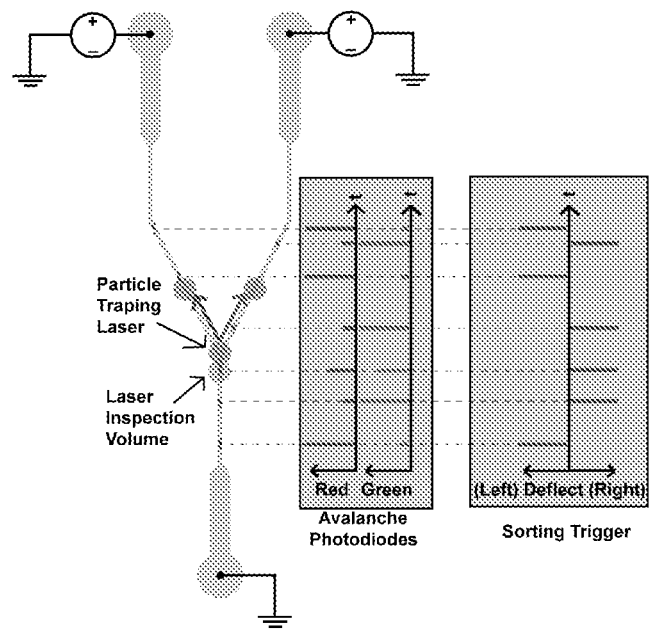

In some cases, electrical sorting may be used in the methods and devices of the present invention for sorting based on simultaneous detection of a plurality of events. For example, simultaneous (i.e. time coincident) detection of two different fluorescence emissions may trigger sorting of a molecule of interest. In some cases, time coincident detection of two different fluorescence emissions may be used to electrically sort chromatin or other complex biomolecules. For example, flow of the chromatin through nanofluidic devices may be induced electrokinetically using voltages applied to reservoirs of the device. The flow rate of molecules inside these devices can be controlled over a wide range with exquisite accuracy. The flow rate can be controlled to an accuracy of about, or better than about 0.00001, 0.00005, 0.0001, 0.0005, 0.001, 0.005, 0.01, 0.05, 0.1, 0.5, 1, 5, 10, 50, 100, 500, 1000, 5000, or 10,000 fL/s or µL/s. The flow rate can be about, less than about, or greater than about 0.00001, 0.00005, 0.0001, 0.0005, 0.001, 0.005, 0.01, 0.05, 0.1, 0.5, 1, 5, 10, 50, 100, 500, 1000, 5000, or 10,000 fL/s or µL/s. This provides not only the opportunity to increase the rates of molecule (e.g. DNA and chromatin) throughput, but it also allows use of an electrical method for rapid single-molecule sorting. A Y-shaped separation chamber (i.e. junction) may be placed immediately following the detection region, the proverbial "fork in the road." Flow rate can be increased and directed preferentially to one branch or the other of the fork by briefly increasing the voltage bias in the corresponding part of the fork. In this way, the molecule is sorted toward the desired path for eventual recapture. This method of control can be applied to any charged molecule such as nucleic acids including DNA or chromatin fragments. For example, the method can be applied to DNA or chromatin fragments bound to antibody-linked fluorophores, which report the epigenetic state, such as fluorophores linked to antibodies to particular methylated proteins (e.g. methylated histones) or DNA sequences, or antibodies to RNA pol II as provided herein. The design of a device using electrical sorting is shown in FIG. 7.

A sorting module utilizing electrokinetic force is shown in FIG. 1. As shown in FIG. 1, electrodes are in electrical contact with the fluidic inlets and outlets of the channels. The sorting actuator can switch the voltage applied to the channels between (a) the inlet and a first outlet and (b) the inlet and a second outlet. If the sorting system has a plurality of branch points, as shown in FIG. 8 (left), the sorting actuator can switch the voltage applied to the channels between the inlet and one of four downstream outlets. In some embodiments, a voltage gradient can be applied to an inlet and more than one outlet. The direction of the voltage gradient can be selected based on the effective charge of the object to be sorted. The magnitude of the voltage gradient can be selected based on a desired object velocity, effective charge of the object, size of the object, conditions of the fluid or buffer surrounding the object, and distance between the electrodes.

The operational or speed limit of the electrically actuated sorting can be dependent on the resistance and capacitance of the channel. Exemplary calculations and measurements of the electrical characteristics of the channel are given in FIG. 30 and FIG. 18. Double layer effects can affect the measured resistance and theoretical resistance of a given system. In an arch-shaped fluidic device, as shown in FIG. 26, a voltage impulse at the input fluidic reservoir can be applied and the current response at one of the output fluidic reservoirs can be measured using a current preamplifier. At a gain setting of $1 \times 10^{-7}$ Amps/volt, the observed steady state ion current can be about or approximately 120 pA. The capacitance-limited switching time can be about 40 microseconds. In some embodiments, the capacitance-limited switching time can be altered by changing the electrical characteristics of the device and the electrical components applying a voltage gradient to the device. For example, the preamp can have a 30 microsecond rise-time limit. The switching time can be about or less than about 0.0001, 0.001, 0.01, 0.01, 0.1, 1, 2, 3, 4, 5, 10, 15, 20, 30, 40, 50, 60, 70, 80, 90, or 100 microseconds. The preamp can have a rise-time limit of about or less than about 0.01, 0.1, 1, 2, 3, 4, 5, 10, 15, 20, 30, 40, 50, 60, 70, 80, 90, or 100 microseconds.

Optical Sorting

Optical sorting involves using an intense laser beam to hold or "tweeze" one or more particles in a medium such as a gas or a liquid. Using an intense infrared laser, to minimize photodamage to the interrogated particles or molecules such as nucleic acids (e.g. DNA or RNA) or proteins, and high numerical aperture optics, to create a tightly confined optical potential well, a fluorophore (e.g. quantum dot)-molecule conjugate may be captured. This technique may be applied by the methods of the present invention inside a device of the present invention. For example, the optical sorting technique may be applied inside a Y-shaped separation chamber and the laser position may be deflected to control the particle trajectory for sorting. Optical sorting can be performed by the methods of the present invention at the single molecule level in the nanofluidic devices of the present invention using the dielectric properties of the fluorophore, particle, or quantum dot. In some cases, this sorting technique may be performed using a constant applied voltage for flow of molecules in a defined direction past the laser. This sorting technique provides ultra-fast sorting—with speeds that can be limited only by fluid forces, not the sorting laser deflection. Forces in the optical potential trap are routinely on the order of 1-1000 pN and, in this case, are applied transverse to the flow direction. Flow velocities in the devices of the present invention, under high-throughput conditions, nominally impart a Stokes drag force of approximately 10 pN on a 20 nm diameter particle. This indicates that deflection of a quantum dot or similarly sized particle in the presence of flow is possible, particularly since deflection into the proper direction requires only a fraction of the possible trapping force. Deflection speeds can extend into the Megahertz range. The methods of the present invention allows for ultra-fast sorting control at rates approaching the fundamental limit inside a fluidic structure. An exemplary design of a device using optical sorting is shown in FIG. 7.

A branched separation chamber of the present invention utilized with either the electrical or optical sorting method may provide an unprecedented level of purity and speed in the recovery of specific molecules of interest including any of the molecules provided herein such as DNA, RNA, chromatin, aptamers, proteins, or peptides. In some embodiments, the triggering event for this sorting method may be based upon the fluorophore (e.g. quantum dot) color signature generated during excitation in the laser inspection volume. The emitted fluorescence may be observed using high-speed, ultra-sensitive avalanche photodetectors such as photodiodes (APDs) or photomultiplier tubes, which output digital signals representing the number of photons observed. To initiate a real-time sorting trigger signal, a programmable high-speed hardware unit may be utilized to perform the rapid decision making process. A field programmable gate array (FPGA) or other logic device known in the art including a digital signal processor or an integrated circuit may be provided to incorporate several operations to make the final sorting decision. The input signal representing fluorescence may be collected using an integrator operation and then buffered to a comparator to decide if a single molecule event has occurred. This operation may be performed for each fluorescence color and corresponding photodetector, simultaneously. When the user-specified condition for sorting is satisfied, the sorting trigger may be output to either the adjustable voltage supply (electrical sorting method) or to the phased array that deflects the infrared laser (optical sorting method).

In another embodiment, the present invention provides a preparative device for preparing molecules (e.g. DNA, RNA, proteins, peptides, aptamers, etc.) by detecting and sorting with single molecule resolution. In some cases, a preparative device of the present invention may incorporate features that allow the sorting of molecules such as chromatin fragments as they are being analyzed. In some cases, chromatin carrying one set of marks (e.g. fluorescent signatures) may be directed into a chamber where they can be recovered for subsequent analysis, and chromatin lacking those marks may be directed into a separate chamber. In some embodiments of the preparative devices of the present invention a junction within the submicrometer channel of the device may provide a bifurcated outflow tract within the device. This device comprising a junction providing a bifurcated outflow tract may provide for directed molecular flow by charging the electrode on one of the two bifurcations of the outflow tract. For example, DNA (e.g. chromatin fragments) may be directed along one or another of the two bifurcations of the outflow tract by the application of a positive charge at the desired outflow tract. In some embodiments of the invention high speed circuitry is provided to switch the charge in real time and in response to the fluorescence characteristics of material in the inspection volume, which lies just before the bifurcation. High speed, real time detection and sorting at the single molecule level are provided to realize a device for studying genomic quantities of DNA.

EXAMPLES

Example 1

Detection

Microfluidics and/or nanofluidics provide an excellent platform for detecting fluorescence emitted from a single molecule. Fluidic channels are constructed in fused silica using a single photolithographic step and capped with silica, as shown in FIGS. 10A and 10B. Near-uniform illumination of the channel cross-section allows for the detection of each and every labeled molecule passing through inspection volume (~150 aL), as shown FIG. 10C. We achieve high signal-to-noise detection in low concentration samples (<10 nM), as shown in FIG. 10D. Until recently, single molecule fluorescence was recorded and analyzed post-experiment using 'homemade' software.

Example 2

Active Sorting and Collection

To replace software-based single molecule detection (SMD), an inexpensive field programmable gate array (FPGA) is implemented, as shown in FIG. 11C. Using a dedicated Altera FPGA operating at 50 MHz, a hardware-level algorithm evaluates single molecule fluorescence at microsecond time scales. Individual molecules are actively sorted and separated in real-time within a bifurcated nanofluidic channel, as shown in FIG. 11A and FIG. 11B based upon parameters such as fluorescence intensity and color.

Figure 12B:
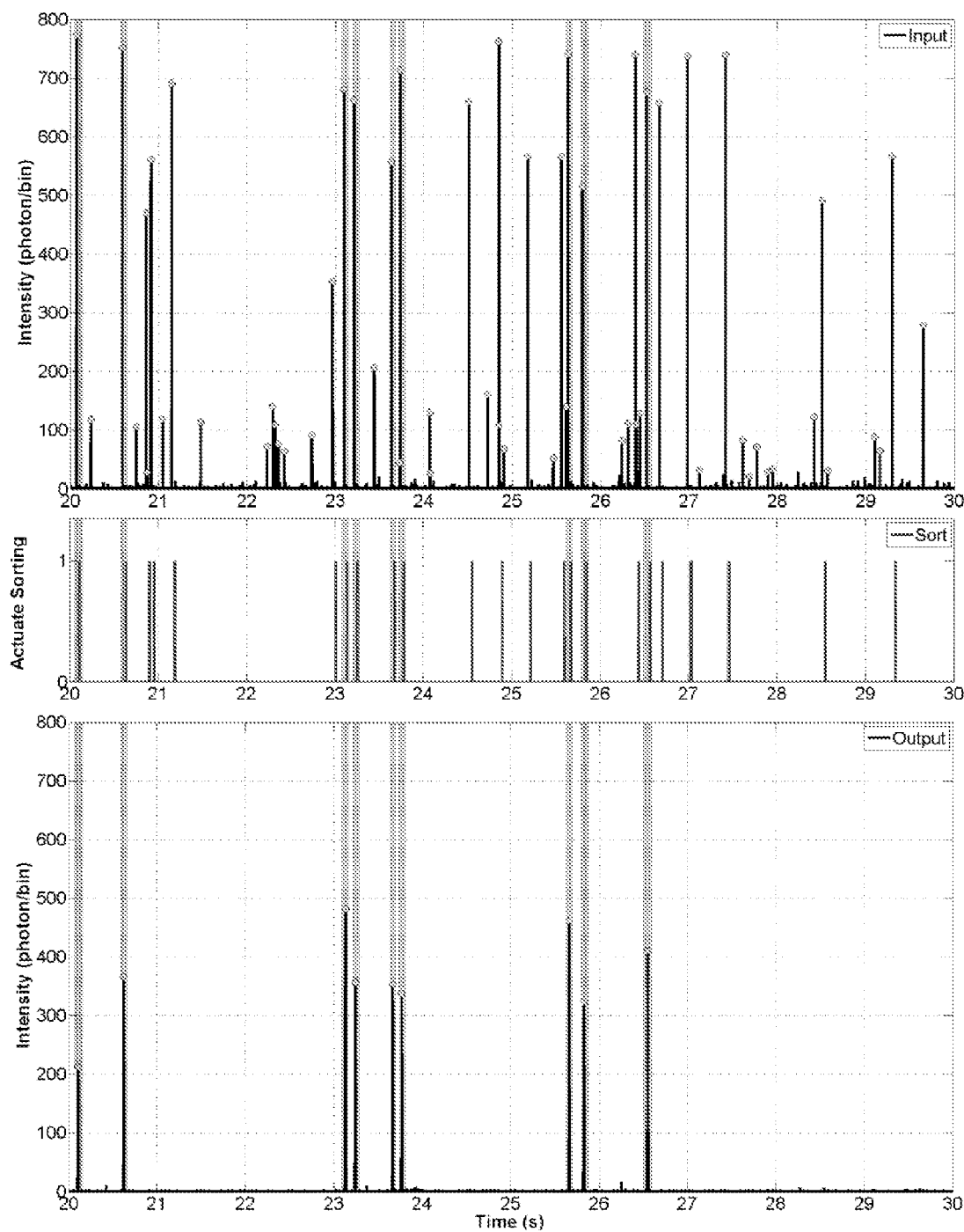
FIG. 12B: depicts time traces illustrating the detection (input), selection (sort), and collection (output) of 10 Kbp fragments from a mixture of 2 and 10 Kbp fragments. An intensity of 150 photons/bin was applied to separate the fragments. The time-traces illustrating the photon detection is the top graph, sorting actuation the middle graph, and output the bottom graph.

FIG. 12A shows parameters and results for an exemplary sorting experiment. FIG. 12B shows results from molecules sorted by a nanofluidic channel. FIG. 12B shows results generated by using a 5.7 Kbp linearized plasmid to test the movement of molecules through a sorting device and to measure the efficiency of recollecting them using a pipette. Samples were transported electrokinetically through 1 branch of the y-shaped junction, collected at the output port using a pipetter, and then amplified using qPCR. The results of qPCR were benchmarked against standards of known concentration to evaluate the 'Quantity collected.' At intervals throughout the experiment, the rate of single molecule events were measured in the y-shaped channel using laser induced florescence in order to 'estimate throughput.' Based upon the 'estimated throughput' and the 'quantity collected' masses, we derive a collection efficiency.

Molecules could be collected using a variety of techniques, including a functionalized membrane, filter paper, an agarose-coated electrode, an absorbent material, or using additional tubing. The additional tubing could lead to an off-chip location.

Example 3

Application to Epigenetics Analysis

Chromatin within eukaryotic cells includes DNA and histone proteins assembled on DNA into the nucleosome. The DNA sequence carries the genetic code and controls inheritance of traits, however, reversible covalent modifications to specific DNA sequences and their associated histones can influence how the underlying DNA is utilized and can therefore also control traits. These have been referred to as modifications of epigenetic state. Epigenetic states are governed by DNA methylation and a host of modifications to histones bound with DNA. These states are essential for proper developmentally regulated gene expression and are perturbed in many diseases. There is great interest in identifying epigenetic mark placement genome-wide and understanding how these marks vary among cell types, with changes in environment or according to health and disease status. A host of modifications exist including methylation, acetylation, ribosylation, phosphorylation, sumoylation, ubiquitylation and citrullination occur at more than 30 amino acid residues of the four core histones within the nucleosome. Given the fundamental role that epigenetic mechanisms play in normal development, environmental responses and how their perturbation affect disease state, there is increasing effort devoted to characterize the human epigenome.

The flow of chromatin through a nanofluidic channel is can facilitate epigenetic analysis. We first demonstrated Single Chromatin Analysis at the Nanoscale (SCAN) to investigate the bound state of nucleosomes in native chromatin fragments. Chromatin from HeLa cells, both wild-type and expressing eGFP-H2B, were admixed in varying proportion. Events demonstrating both a green histone mark and a red DNA stain were used to verify the in-tact chromatin structure during flow. A second experiment showed SCAN's utility with existing probes for epigenetic marks. Using a green-labeled methyl-binding domain (MBD) protein and red DNA stain, we identified DNA methylation, an epigenetic mark.

Figures 13, 14:
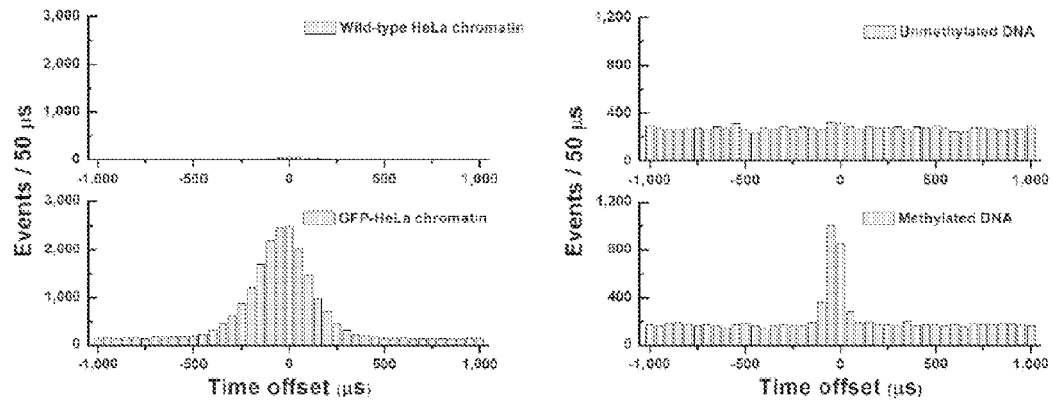
FIG. 13: shows a graph (left) depicting recovery of GFP labeled HeLa chromatin and wild-type HeLa chromatin and a graph (right) depicting recovery of MBD-methylated DNA and unmethylated DNA. The left graph shows bound nucleosomes on chromatin were detected in proportion to the amount of GFP-Hela chromatin present. The right graph shows bound complexes of MBD-methylated DNA were detected above a constant-level background of uncorrelated molecules.
FIG. 14: shows a table depicting detection throughput.

FIG. 14 shows a table characterizing the detection throughput of an embodiment of the sorting system described herein.

We have demonstrated SCAN, a nanofluidic-based SMD method for studying the bound state of nucleosomes to native chromatin and for interrogating epigenetic state using bound MBD-DNA complexes. This technology could provide a significant improvement over conventional ChIP, enabling simultaneous detection of multiple epigenetic marks on a single molecule. SCAN can be further enhanced using a bifurcated channel design and a dedicated FGPA to achieve real-time single molecule detection and sorting. We have shown the ability to separate, collect, and amplify (qPCR) sorted material. The present invention also provides a complete system for performing rapid epigenomic analysis using SCAN-sort with initial throughput on the order of 10 Mbp/min in a single fluidic channel.

Example 4

Single Molecule Sorting

A system was designed, as described herein, to extend fluidic-based single molecule techniques to provide rapid selection of individual molecules that match a specific profile or molecule 'signature.' The system was designed with the following principles in mind: To collect and identify the 'signature' of a single molecule, as measured from fluorescence or other detectable means, in real-time; to decide if that molecule's signature matches a user-defined sorting or selection criteria; to actuate the physical process of collecting pattern-matched molecules; and to collect these molecules for subsequent analysis (i.e. PCR, sequencing, etc).

Figure 15:
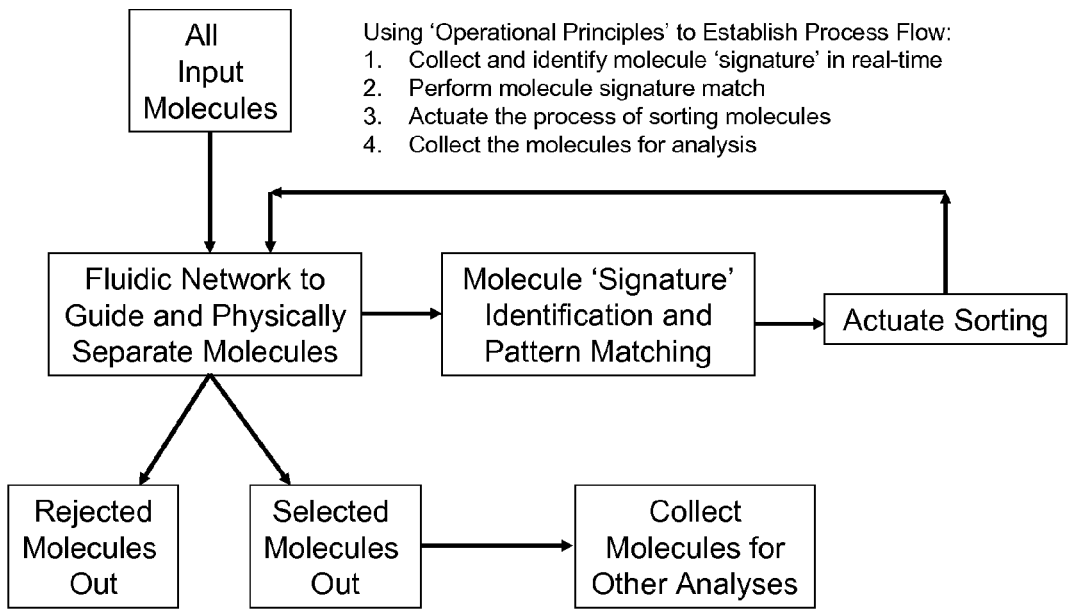
FIG. 15: shows a conceptual layout for sorting molecules.
Figure 16:
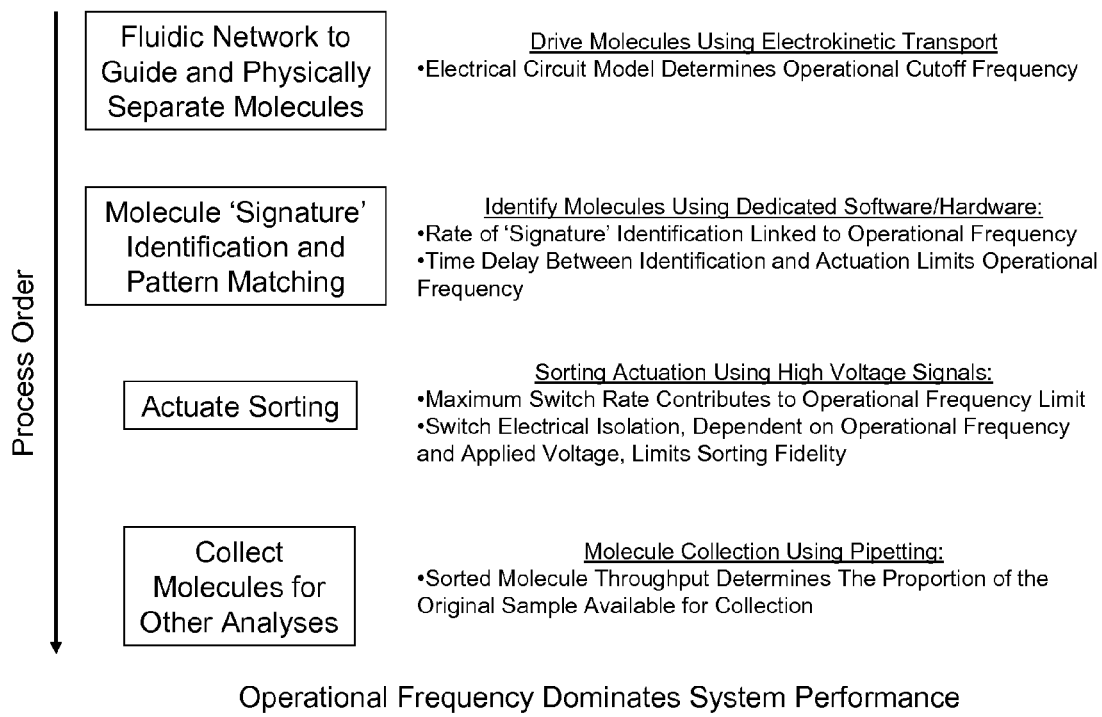
FIG. 16: depicts a flow chart illustrating processing order of the present invention.
Figure 17:
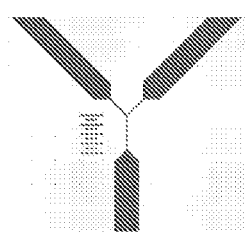
FIG. 17: shows an electrical representation of a bifurcated fluidic network.
Figure 17:
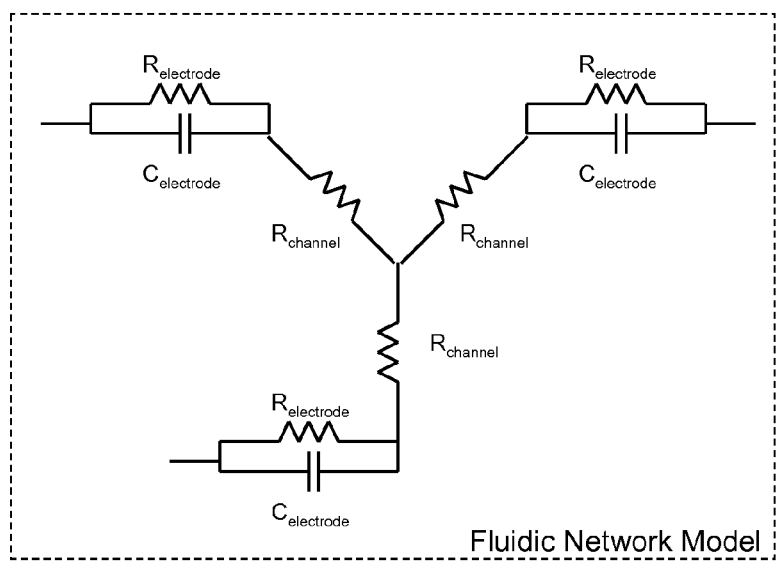

The system can have the following possible applications: Collection of chromatin fragments with specific epigenetic marks (SCAN-sort), Purification of aptamer probes with highest binding affinity (SELEX-FAAS), Drug discovery and assembly of protein or DNA libraries, and Alternative to gel-electrophoresis and excise to recover selected fragments. FIG. 15 shows a schematic of the conceptual layout. FIG. 16 shows the sorting sub-systems and rate determining steps. FIG. 17 shows a circuit model of a bifurcated fluidic network. The fluidic network can guide and physically separate molecules. FIG. 18 shows equations and calculations to determine the resistive characteristics of the channels. FIG. 19 shows a manner for controlling the bifurcated fluidic network. The effective resistance can be reduced using a parallel network of external resistors. This can also allow for increased control over flow characteristics. In some embodiments, the resistance can be reduced while accounting for the increase in heat losses.

Figure 20:
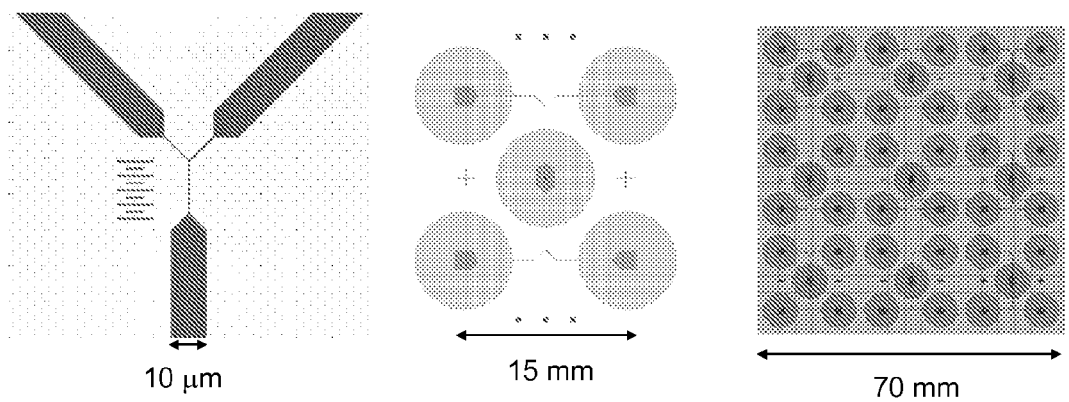
FIG. 20: shows a progression of size scale for different devices, including a microfluidic channel at 10 µm (left).

FIG. 20 shows an improvement in design of fluidic networks by moving to single layer lithography. This can reduce device clogging, and eliminate resistive network misbalance.

Figure 21:
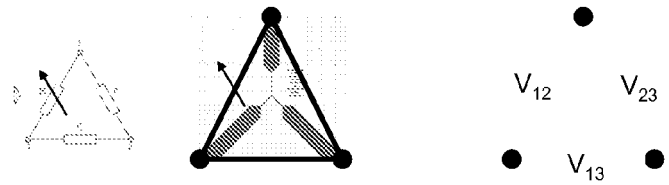
FIG. 21: is a schematic of two networks utilizing variable resistors.
Figure 21:
Figure 22A:
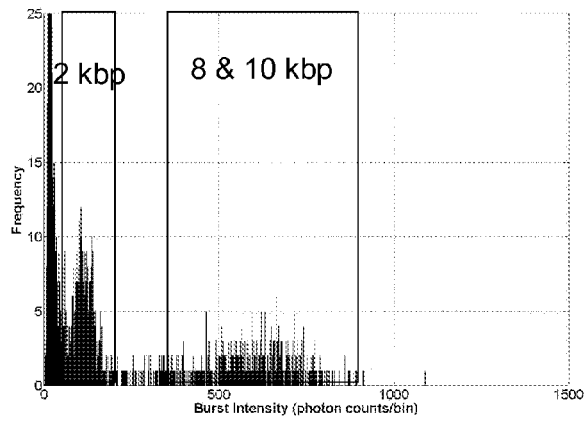
FIG. 22: shows a schematic of an experiment to separate 2, 8, and 10 kbp DNA using a fluidic network (right), and corresponding frequency of DNA fragments as a function of burst intensity (left).
Figure 22B:
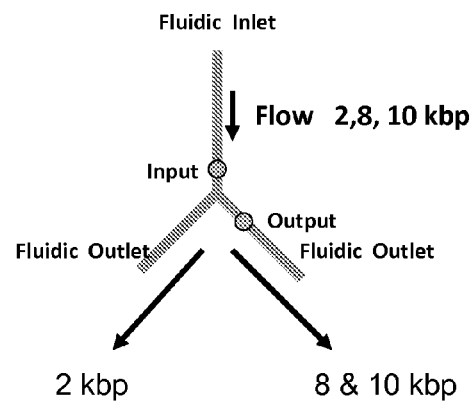

FIG. 21 shows one way to tune the resistive network using variable resistors. FIG. 22 shows removal of a 2 kbp DNA fragment from a mixture of 2, 8, and 10 kbp fragments. Here, the experiment is can be performed by marking all fragments with YOYO-1 intercalator and identifying larger fragments using differences in fluorescence intensity. Real-time selection can be performed using electrically-actuated sorting hardware and verify sorting accuracy immediately after sorting occurs.

FIG. 23 shows a schematic of molecule sorting hardware utilizing variable resistors.

Figure 24:
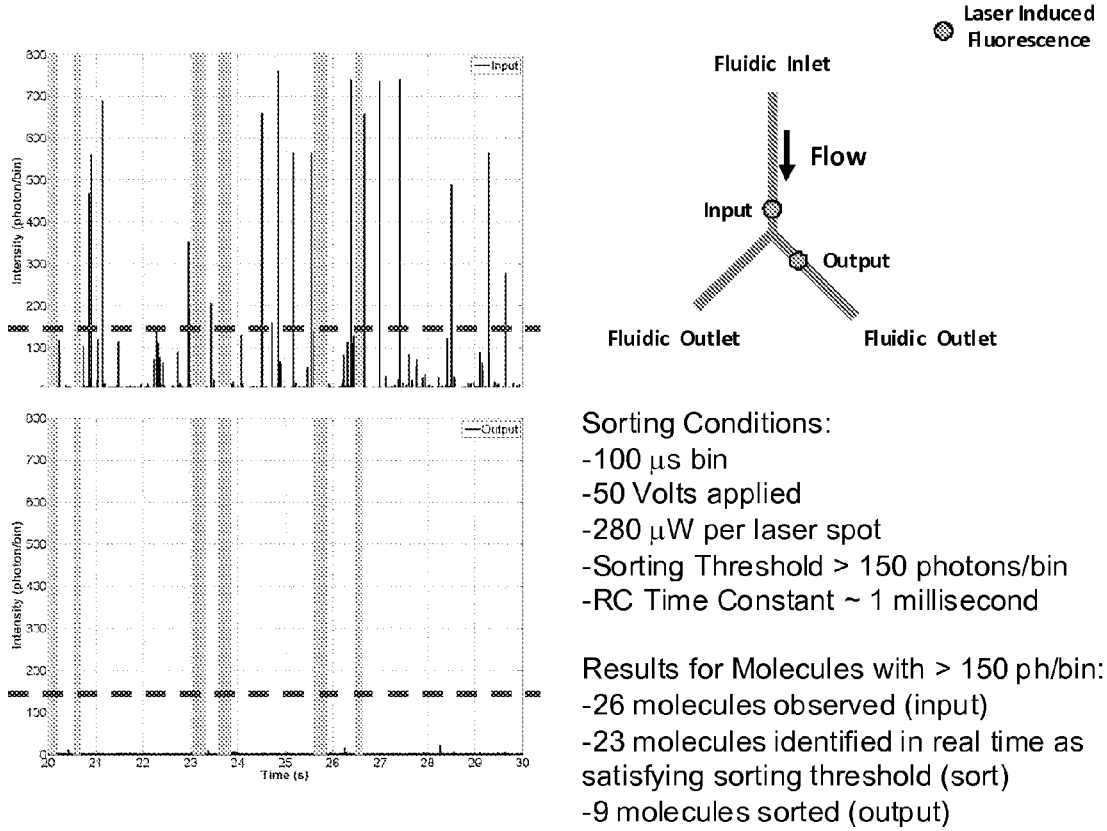
FIG. 24: shows a 10 second example of sorting. The sorting conditions are as follows: 100 µs bin, 50 Volts applied, 280 µW per laser spot, Sorting threshold >150 photons/bin, and RC time constant ~1 millisecond. The results for molecules with >150 ph/bin were as follows: 26 molecules observed (input), 23 molecules identified in real time as satisfying sorting threshold (sort), 9 molecules sorted (output).

FIG. 24 shows an example of sorting using the hardware described in this example.

FIG. 25 shows the relational advantages of solid state relays and reed relays. In some embodiments, fluidic channel dimensions can be adjusted, and solid state relays can be used. /use of solid state relays can reduce operating voltages and/or allow the use of faster relays.

Example 5

Time-Correlation Between Input and Output Interrogation Volumes

Figure 33:
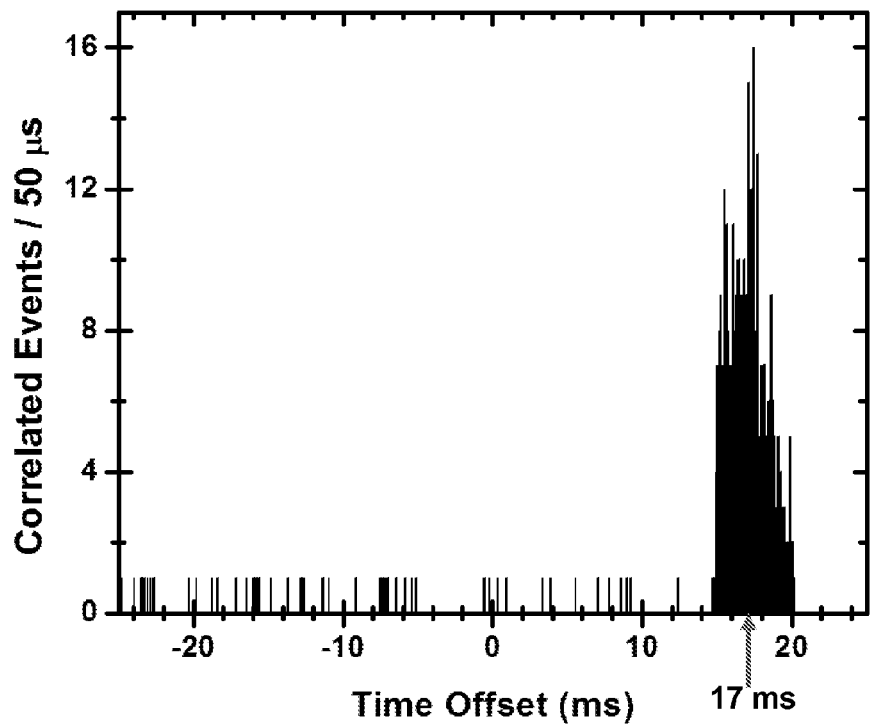
FIG. 33: shows a graph of correlated events in a 50 microsecond bin as a function of time offset.
Figure 34:
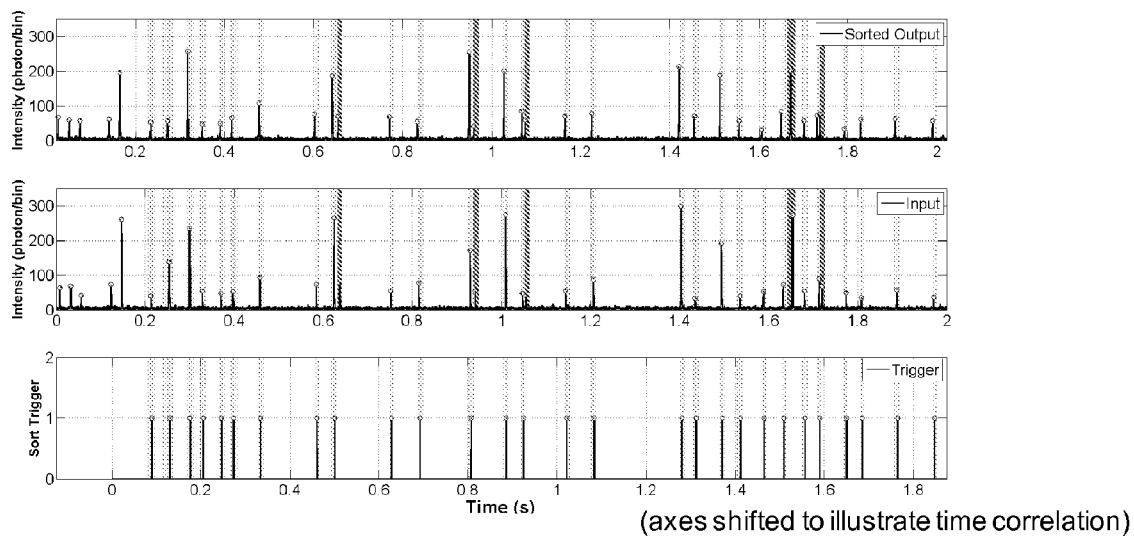
FIG. 34: shows an example of high speed sorting. The top graph is the photons measured in the sorted output. The middle graph is the photons measured in the input. The bottom graph shows the actuation of the sorting trigger.

Objects passing between an input interrogation volume and an output interrogation volume were detected. FIG. 33 shows number of correlated events in a 50 microsecond bin as a function of a time offset. As shown in FIG. 33, the time offset between the input and output interrogation volumes is about 17 ms.

Example 6

Time-Correlated Sorting

Figure 32:
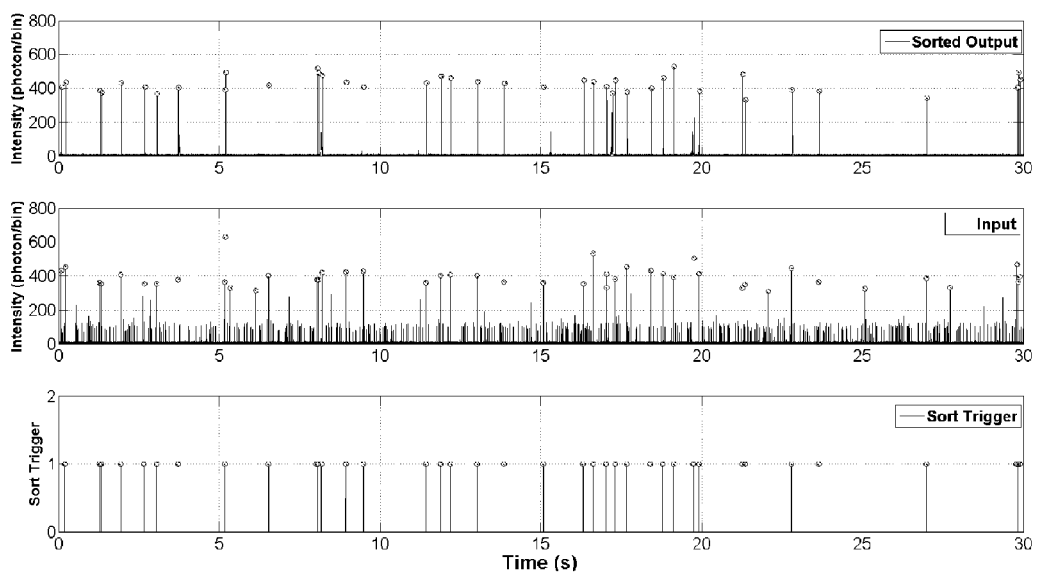
FIG. 32: shows an example of time-correlated sorting. The top graph is the photons measured in the sorted output, the middle graph is the photons measured in the input, and the bottom graph is the actuation of the sort trigger.

A sample comprising a mixture of 2 and 8 Kbp fragments was flowed through a sorting device. The fragments were flowed using a +20 V gradient. As shown in FIG. 32, 95 molecules were detected at the input using a threshold of 300 photons per bin. 78 molecules were identified by the sort trigger, using a trigger pulse of greater than 17 ms. 76 molecules were collected at the sorted output.

Example 7

High Speed Sorting

High speed sorting was performed using a sorting device. A sample comprising a mixture of 2 and 8 Kbp fragments was delivered to an input channel. The sample was driven using a +20V gradient. 1023 molecules above the threshold (between 25-300 photons/bin) were detected at the input. 757 molecules were identified by the sorting trigger, using a trigger pulse of 25 ms. 1063 molecules were collected at the sorted output channel.

A long trigger pulse duration can connect molecules that occur in rapid succession. In this example, perfect, or almost perfect collection of all molecules satisfying the threshold was achieved, but only 28 of the 33 were identified in the trigger signal trace because the algorithm does not issue a new pulse when multiple molecules occur within a trigger window.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for sorting chromatin comprising:
    (a) a channel that is fluidically connected to a plurality of downstream flow paths, said channel being adapted to hold said chromatin in a continuous liquid body in said channel;
    (b) one or more light sources configured to illuminate the channel to create one or more interrogation volumes, wherein the one or more interrogation volumes are bounded by a submicrometer channel region of said channel, and wherein the one or more interrogation volumes are each less than 0.5 femtoliters;
    (c) a detection module configured to detect at least two types of signals indicative of two distinct properties of the chromatin in the one or more interrogation volumes;
    (d) a sorting module configured to direct the chromatin to one of the plurality of downstream flow paths based on the two distinct properties indicated by said two types of signals; and
    (e) one or more electrodes in electrical connection by fluid with the channel and downstream flow paths to direct the chromatin.

2. The system of claim 1, further comprising:
    (a) one or more secondary light sources configured to illuminate one of the plurality of downstream flow paths to create one or more downstream interrogation volumes; and
    (b) a secondary detection module configured to detect at least one type of signals in the one or more downstream interrogation volumes.

3. The system of claim 2, further comprising a secondary sorting module configured to direct the chromatin to one of a plurality of secondary downstream flow paths based on said two types of signals in the one or more downstream interrogation volumes, wherein the plurality of secondary downstream flow paths are different from the plurality of downstream flow paths of (a).

4. A method for sorting an object in a channel, comprising:
    (a) flowing the object through said channel, wherein said object is labeled with a plurality of labels;
    (b) illuminating the channel to create one or more interrogation volumes, each of which is confined by walls of a submicrometer channel region of said channel and a beam of light, and wherein each of said one or more interrogation volumes has a volume of less than 0.5 femtoliters; and
    (c) detecting a first label and a second label of said plurality in the same or distinct interrogation volumes of said one or more interrogation volumes to generate time-correlated resolution of said first and second label, wherein the first label is indicative of a first property of the object and the second label is indicative of a second property of the object; and
    (d) directing the object to one of a plurality of downstream flow paths that are fluidically connected to said channel, wherein the object is directed based on the first property and the second property, and wherein the object is directed by electrodes in electrical connection by fluid with the channel and downstream flow paths.

5. The method of claim 4, further comprising:
    (a) illuminating a downstream pathway to create one or more downstream interrogation volumes; and
    (b) detecting at least one label of said plurality in the one or more downstream interrogation volumes.

6. The method of claim 5, further comprising directing the object to one of a plurality of secondary downstream flow paths based on said detecting at least one label in the one or more downstream interrogation volumes, wherein the plurality of secondary downstream flow paths are different from the plurality of downstream flow paths of (d).

7. The method of claim 4, wherein the object is a chromatin.

8. The system of claim 1, wherein the one or more interrogation volumes are each less than 0.2 femtoliters.

9. The system of claim 1, wherein the sorting module has a switching time that is less than 100 microseconds.

10. The system of claim 1, wherein the one or more electrodes are capable of imparting an electrokinetic force on the object.

11. The system of claim 1, wherein the channel and each of the plurality of downstream flow paths has a width less than 1 μm.

12. The system of claim 1, wherein the channel and the plurality of downstream flow paths each has a width less than 1 μm and a height less than about 1 μm.

13. The method of claim 4, wherein the one or more interrogation volumes are each less than 0.2 femtoliters.

14. The method of claim 4, wherein the object is directed by a switching module having a switching time that is less than 100 microseconds.

15. The method of claim 4, wherein the object is directed by electrokinetic force using the electrodes.

16. The method of claim 4, wherein the channel and each of the plurality of downstream flow paths has a width less than 1 μm.

17. The method of claim 4, wherein the channel and the plurality of downstream flow paths each has a width less than 1 μm and a height less than 1 μm.

18. The method of claim 4, wherein the object is a chromatin, and the first label is complexed with an epigenetic marker on the chromatin and the second label is complexed with a protein or nucleotide of the chromatin.

19. The method of claim 4, wherein the object is directed less than 0.001 seconds after the first label and second label are detected.

20. A method for sorting an object in a channel, comprising:
    (a) flowing the object through said channel, wherein said object is labeled with a plurality of labels;
    (b) illuminating the channel to create one or more interrogation volumes, wherein each of said one or more interrogation volumes is confined by walls of a submicrometer channel region of said channel and a beam of light, and each of said one or more interrogation volumes has a volume of less than 0.5 femtoliters; and
    (c) detecting a first label and a second label of said plurality of labels in the same or distinct interrogation volumes of said one or more interrogation volumes to generate time-correlated resolution of said first label and second label, wherein the first label is indicative of a first property of the object and the second label is indicative of a second property of the object; and (d) directing the object to one of a plurality of downstream flow paths that are fluidically connected to said channel, wherein the object is directed based on the first property and the second property, and further wherein the object is directed less than 0.001 seconds after the first label and second label are detected.

21. The method of claim 20, wherein the channel and the plurality of downstream flow paths each have a width less than 1 μm and a height less than 1 μm.

22. The system of claim 1, wherein a branch point of the plurality of downstream flow paths is positioned at or immediately downstream of the detection module.

23. The system of claim 1, wherein the system is configured such that the sorting module directs the chromatin to one of the plurality of downstream flow paths in less than 0.001 seconds after the at least two types of signals are detected by the detection module.

\* \* \* \* \*

UNITED STATES PATENT AND TRADEMARK OFFICE
CERTIFICATE OF CORRECTION

PATENT NO. : 9,605,298 B2
APPLICATION NO. : 13/389259
DATED : March 28, 2017
INVENTOR(S) : Harold G. Craighead et al.

It is certified that error appears in the above-identified patent and that said Letters Patent is hereby corrected as shown below:

In the Specification

Column 1, delete Lines 19-22 and replace with the following:
--This invention was made with government support under grant number DA025722 awarded by the National Institutes of Health and grant number 9876771 awarded by the National Science Foundation. The government has certain rights in the invention.--

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*